(12) United States Patent
Boundy-Mills et al.

(10) Patent No.: US 10,196,663 B2
(45) Date of Patent: Feb. 5, 2019

(54) METHODS OF PRODUCING GLYCOLIPIDS

(71) Applicant: The Regents of the University of California, Oakland, CA (US)

(72) Inventors: Kyria Boundy-Mills, Davis, CA (US); Luis Antonio Garay Almada, Sacramento, CA (US); Irnayuli Sitepu, Davis, CA (US); J. Bruce German, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/275,075

(22) PCT Filed: Mar. 30, 2015

(86) PCT No.: PCT/US2015/023370
§ 371 (c)(1),
(2) Date: Sep. 23, 2016

(87) PCT Pub. No.: WO2015/153476
PCT Pub. Date: Oct. 8, 2015

(65) Prior Publication Data
US 2017/0183702 A1   Jun. 29, 2017

Related U.S. Application Data

(60) Provisional application No. 61/973,195, filed on Mar. 31, 2014.

(51) Int. Cl.
*C12P 19/44* (2006.01)
*C12N 1/16* (2006.01)
*C12P 7/64* (2006.01)
*C12R 1/645* (2006.01)
*C07H 15/06* (2006.01)

(52) U.S. Cl.
CPC .............. *C12P 19/44* (2013.01); *C07H 15/06* (2013.01); *C12N 1/16* (2013.01); *C12P 7/64* (2013.01); *C12R 1/645* (2013.01)

(58) Field of Classification Search
None
See application file for complete search history.

(56) References Cited

U.S. PATENT DOCUMENTS

| | | | |
|---|---|---|---|
| 4,215,213 A | 7/1980 | Inoue et al. | |
| 4,297,340 A | 10/1981 | Abe et al. | |
| 5,417,879 A | 5/1995 | Hall et al. | |
| 5,756,471 A | 5/1998 | Hillion et al. | |
| 5,981,497 A | 11/1999 | Maingault | |
| 8,530,206 B2 * | 9/2013 | Develter | C12N 15/01 435/134 |
| 8,642,793 B1 | 2/2014 | Kim et al. | |
| 8,642,794 B1 | 2/2014 | Kim et al. | |
| 2006/0199244 A1 | 9/2006 | Ashby et al. | |
| 2011/0136110 A1 * | 6/2011 | Van Bogaert | C12N 15/01 435/6.1 |
| 2011/0237531 A1 | 9/2011 | Yanagisawa et al. | |
| 2012/0022241 A1 | 1/2012 | Gross et al. | |
| 2012/0080116 A1 | 4/2012 | Chouinard | |
| 2013/0072414 A1 | 3/2013 | Price et al. | |
| 2013/0085067 A1 | 4/2013 | Schofield et al. | |
| 2013/0089892 A1 | 4/2013 | Soetaert et al. | |
| 2013/0092421 A1 | 4/2013 | Kajiya | |

FOREIGN PATENT DOCUMENTS

| | | |
|---|---|---|
| EP | 0 209 783 A1 | 1/1987 |
| WO | WO 2012/080116 | 6/2012 |
| WO | WO 2013/092421 | 6/2013 |
| WO | WO 2015/075443 | 5/2015 |
| WO | WO 2015/142736 | 9/2015 |
| WO | WO 2015/153476 | 10/2015 |
| WO | WO 2017/184884 A1 | 10/2017 |

OTHER PUBLICATIONS

PCT International Preliminary Report on Patentability and Written Opinion dated Oct. 13, 2016 issued in PCT/US2015/023370.
Wang et al. (2016) "Phylogenetic classification of yeasts and related taxa within Pucciniomycotina," Studies in Mycology, 81:149-189.
PCT International Search Report and Written Opinion dated Jul. 15, 2015 issued in PCT/US2015/023370.
PCT International Search Report and Written Opinion dated Jul. 14, 2017 issued in PCT/2017/028670.
Boundy-Mills, et al., "Carbon source utilization and toxin tolerance of *oleaginous* yeasts" *Symposium on Biotechnology for Fuels and Chemicals*, Poster No. 26692, Conference Dates Apr. 28-May 1, 2014.
Boundy-Mills, et al., "Structure and surfactant activities of glycolipids secreted by *basidiomycetous* yeasts" *Symposium on Biotechnology for Fuels and Chemicals*, Poster No. 32036, Conference Dates Apr. 25-28, 2016.
Cajka, et al., "Multiplatform Mass Spectrometry-Based Approach Identifies Extracellular Glycolipids of the Yeast *Rhodotorula babjevae* UCDFST 04-877" *Journal of Natural Products*79(10):2580-2589, 2016.
Deinema, Maria H., "Intra- and Extra-Cellular Lipid Production by Yeasts" *Meded. Landbouwhogeschool, Wageningen* 61(2):1-54, 1961.
Garay, et al., "Eighteen new *oleaginous* yeast species" *Symposium on Biotechnology for Fuels and Chemicals*, Poster No. 32030, Conference Dates Apr. 25-28, 2016.
Garay, et al., "Eighteen new *oleaginous* yeast species" *Journal of Industrial Microbiology & Biotechnology* 43(7):887-900, Jul. 2016.
Garay, et al., "Discovery and synthesis and secretion of polyol esters of fatty acids by four *basidiomycetous* yeast species in the order Sporidiobolales" *Journal of Industrial Microbiology & Biotechnology* 44(6):923-936, Jun. 2017.
Garay, et al., "Simultaneous production of intracellular polyol esters of fatty acids by *Rhodotorula babjevae* and *Rhodotorula* aff. Paludigena" *Journal of Industrial Microbiology & Biotechnology* pp. 1-17, Jul. 2017.
Haferburg, et al., "Extracellular microbial lipids as biosurfactants" *Advances in Biochemical Engineering/ Biotechnology* 33:53-93, 1986.

(Continued)

*Primary Examiner* — Vera Afremova
(74) *Attorney, Agent, or Firm* — O'Banion & Ritchey LLP; John P. O'Banion; Jennifer L. Wahlsten

(57) ABSTRACT

Provided are methods and yeast cultures for producing glycolipids and glycolipid compositions.

40 Claims, 4 Drawing Sheets

(56) References Cited

OTHER PUBLICATIONS

Johnson, et al., "Bioemulsifier production by *oleaginous* yeast *Rhodotorula glutinis* IIP-30" *Biotechnology Letters* 14(6):487-490, Jun. 1992.

Kurosawa, et al., "Extracellular Accumulation of the Polyol Lipids, 3, 5-Dihydroxydecanoyl and 5-Hydroxy-2-decenoyl Esters of Arabitol and Mannitol, by *Aureobasidium* sp" *Biosci. Biotechnol. Biochem.* 58(11):2057-2060, 1994.

Ma, et al., "Sophorolipid production from delignined corncob residue by *Wickerhamiella domercqiae* var. sophorolipid CGMCC 1576 and *Cryptococcus curvatus* ATCC 96219." *Appl Microbiol Biotechnol* 98(1):475-483, Jan. 2014.

Price, et al., "Structural characterization of novel extracellular liamocins (mannitol oils) produced by *Aureobasidium pullulans* strain NRRL 50380". *Carbohydrate Research* 370:24-32, 2013.

Ruinen, et al., "Composition and properties of the extracellular lipids of yeast species from the phyllosphere" *Antonie van Leeuwenhoek* 30:377-384, 1964.

Sitepu, et al., "Manipulation of culture conditions alters lipid content and fatty acid profiles of a wide variety of known and new *oleaginous* yeasts species" *Bioresour. Technol.* 144:1-23, 2013.

Sitepu, et al., "Lipid accumulation by *oleaginous* yeasts in synthetic and authentic AFEX corn stover hydrolysate" *Symposium on Biotechnology for Fuels and Chemicals*, Poster No. 26756, Conference Dates Apr. 28-May 1, 2014.

Sitepu, et al., "Oleaginous yeasts for biodiesel: Current and future trends in biology and production" *Biotechnology Advances* 32(7):1336-1360, Nov. 2014.

Tulloch, et al., "Extracellular Glycolipids of Rhodotorula Species: The Isolation and Synthesis of 3-D-Hydroxypalmitic and 3-D-Hydroxystearic Acids[1]" *Canadian Journal of Chemistry* 42:830-835, 1964.

ATCC, Rhodosporidiobolus ruineniae (Holzschu et al.) Wang et al. (ATCC ® 36398™), https://www.atcc.org/Products/All/36398.aspx , May 23, 2018.

Cameo Chemicals, Product insert, "Dodecanol", Jun. 1999.

chemicalland21.com, "Lauryl Alcohol", http://chemicalland21.com/industrialchem/solalc/LAURYL&20ALCOHOL.htm , May 20, 2018.

Garay et al., "Extracellular fungal polyol lipids: A new class of potential high value lipids," Biotechnol. Adv., Mar.-Apr. 2018, vol. 36, No. 2, pp. 397-414. <doi:10.1016/j.biotechadv.2018.01.003>.

Garay et al., "Discovery of synthesis and secretion of polyol esters of fatty acids by four *basidiomycetous* yeast species in the order Sporidiobolales," Journal of Industrial Microbiology & Biotechnology,vol. 44, No. 6, Jun. 2017, pp. 923-936.

IPSC INCHEM, "1-Dodecanol" http://inchem.org/documents/icsc.icsc.eics1765.htm , May 20, 2018.

Kitamoto, et al., "Intracellular accumulation of mannosylerythritol lipids as storage materials by Candida Antarctica" *Appl Microbiol Biotechnol* 36:768-772, 1992.

National Center for Biotechnology Information. PubChem Compound Database; CID=8193, http://pubchem.ncbi.nlm.nih.gov/compound/8193 , May 20, 2018.

Pseudohyphozyma Bogoriensis, https://www.ncbi.nlm.nih.gov/Taxonomy/Browser/wwwtax.cgi , Jun. 13, 2018.

Moesziomyces Antarcticus, https://www.ncbi.nlm.nih.gov/Taxonomy/Browser/wwwtax.cgi?mode=Info&id=84753&lv , Jul. 17, 2018.

Rhodosporidium=Rhodotorula, https://www.ncbi.nlm.nih.gov/Taxonomy/Browser/wwwtax.cgi , Jun. 13, 2018.

Rhodotorula Babjevae, https://www.ncbi.nlm.nih.gov/Taxonomy/Browser/wwwtax.cgi , Jun. 13, 2018.

Rhodotorula Diobovata, https://www.ncbi.nlm.nih.gov/Taxonomy/Browser/wwwtax.cgi , Jun. 13, 2018.

Rhodotorula Kratochvilovae, https://www.ncbi.nlm.nih.gov/Taxonomy/Browser/wwwtax.cgi , Jun. 13, 2018.

Rhodotorula Paludigena, https://www.ncbi.nlm.nih.gov/Taxonomy/Browser/wwwtax.cgi , Jun. 13, 2018.

Rhodotorula Sphaerocarpa, https://www.ncbi.nlm.nih.gov/Taxonomy/Browser/wwwtax.cgi , Jun. 13, 2018.

Rhodosporidiobolus Colostri, https://www.ncbi.nlm.nih.gov/Taxonomy/Browser/wwwtax.cgi?id=231213 , Jul. 19, 2018.

Rhodotorula Dairenensis, https://www.ncbi.nlm.nih.gov/Taxonomy/Browser/wwwtax.cgi , Jun. 13, 2018.

Rhodosporidiobolus Ruineniae, bttps https://www.ncbi.nlm.nih.gov/Taxonomy/Browser/wwwtax.cgi , Jun. 13, 2018.

Rhodosporidiobolus Nylandii, https://www.ncbi.nlm.nih.gov/Taxonomy/Browser/wwwtax.cgi , Jun. 13, 2018.

Sporidiobolales, https://www.ncbi.nlm.nih.gov/Taxonomy/Browser/wwwtax.cgi?id=231213 , Jul. 19, 2018.

Wikipedia, "Dodecanol", https://en.wikipedia.org/wiki/Dodecanol, May 20, 2018.

* cited by examiner

METHODS OF PRODUCING GLYCOLIPIDS

CROSS-REFERENCE TO RELATED APPLICATIONS

This application is the U.S. National Entry under 35 U.S.C. § 371 of Intl. Appl. No. PCT/US2015/023370, filed on Mar. 30, 2015, which claims the benefit of priority under 35 U.S.C. § 119(e) of U.S. Provisional Application No. 61/973,195, filed on Mar. 31, 2014, which are hereby incorporated herein by reference in their entireties.

FIELD

Provided are methods and yeast cultures for producing glycolipids and glycolipid compositions.

BACKGROUND

Glycolipids such as sophorolipids (SL) are environmentally friendly and renewable biosurfactants used in detergents and other consumer and industrial products. Sophorolipids are amphiphilic molecules comprising a disaccharide of glucose in the form of sophorose, attached to a fatty acyl moiety, which can be either in the free acidic form, or in the cyclic lactone form (See, FIG. 2). *Starmerella bombicola* ATCC 22214, an ascomycetous yeast which has been thoroughly studied for SL production [1-3], synthesizes a mixture of several structurally related SL molecules, where the sophorose moiety is linked to the fatty acyl chain in the ω-1 carbon. SL from ascomycetous yeast *Starmerella bombicola* is commercially produced and utilized in consumer and industrial products, but commercialization is limited to high-end products due to high production costs.

SL synthesis by fermentation with yeast species *Starmerella bombicola* requires both a carbohydrate and a hydrophobic substrate such as a purified fatty acid or vegetable oil [4]. SL secretion is less than one g/L when fed 100 g/L glucose with no hydrophobic substrate [5]. Higher yields require energetically costly and expensive substrates, such as oleic acid or canola oil. Therefore, the *S. bombicola* process is only economically viable for relatively high value products such as detergents and emulsifiers.

Fourteen yeast species have been reported to produce and secrete glycolipids known as sophorolipids (SL) in industrially relevant amounts (at least 1 g/L, see Table 1):

TABLE 1

Yeast Species Reported To Produce And Secrete Commercially Relevant Amounts Of Sophorolipids

| Species | Year of publication | Reference |
|---|---|---|
| Candida albicans | 2012 | [6] |
| Candida apicola (syn. Torulopsis magnoliae) | 1961 | [7, 8] |
| Candida batistae | 2008 | [9] |
| Candida floricola | 2010 | [10] |
| Candida gropengiesseri (syn. Torulopsis gropengiesseri) | 1967 | [11] |
| Candida kuoi | 2010 | [12, 13] |
| Candida riodocensis | 2010 | [12] |
| Candida stellata | 2010 | [12] |
| Cyberlindnera samutprakarnensis | 2013 | [14] |
| Rhodotorula bogoriensis | 1968 | [15] |
| Starmerella bombicola (syn. Candida bombicola) | 1970 | [16-19] |

TABLE 1-continued

Yeast Species Reported To Produce And Secrete Commercially Relevant Amounts Of Sophorolipids

| Species | Year of publication | Reference |
|---|---|---|
| Wickerhamiella domercqiae | 2006 | [20] |
| Wickerhamomyces anomalus (syn. Pichia anomala) | 2008 | [21] |
| Yarrowia lipolytica (syn. Torulopsis petrophilum) | 1984 | [22] |

All of the previously known SL producing yeasts belong to the phylum Ascomycota except one: *Pseudohyphozyma bogoriensis*, (syn. *Rhodotorula bogoriensis*), a yeast belonging to the phylum Basidiomycota, class Microbotryomycetes, in an unclassified clade that includes *R. buffonii* and *R. pustula* [23-25]. This species is not in the order Sporidiobolales. All SL producing yeasts previously known require provision of both a carbohydrate such as glucose, and a hydrophobic substrate such as vegetable oil, fatty acids, alkanes or tryacylglycerols in order to produce commercially useful quantities of glycolipids. U.S. Pat. Nos. 3,205,150 and 3,312,684 describe production of glycolipids (referred to in both patents as glycosides of hydroxyl fatty acids) via a fermentation process using the osmophilic yeast *Torulopsis magnoliae* (syn. *Candida apicola*), an ascomycete yeast species, where a carbohydrate and a nitrogen source is added to the culture to enhance yeast growth, and then a hydrophobic substrate is added to promote production of such compounds. U.S. Pat. No. 4,297,340 uses *C. bombicola* (syn. *Starmerella bombicola*), another ascomycete yeast, and beef tallow as a hydrophobic substrate using a similar method to produce glycolipids which were further derivatized as glycolipid esters to create improved moisturizers for cosmetic purposes. U.S. Pat. No. 5,616,479 uses *S. bombicola* and improved prior art by including fed-batch additions of esters of oils and fatty acids, and recovering the product by settling and water washing, during controlled intervals where agitation and aeration are stopped. More recent patents using glycolipids from *S. bombicola* as microbial protein inducer still undergo the same production method using hydrophobic substrates to create glycolipids (see Intl. Publ. No. WO 2007/073371 A1). The main disadvantage of the previous art is that it requires dosing of hydrophobic substrates during the fermentation, increasing the cost and adding complexity to the recovery of the product.

SUMMARY

In one aspect, a yeast culture is provided. In varying embodiments, the yeast culture comprises a population of basidiomycetous yeast cells, one or more hydrophilic (e.g., non-hydrophobic) carbon sources, and/or at least about 1 g/L glycolipid (e.g., sophorolipid), e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L glycolipid, e.g., up to about 450 g/L of glycolipid, wherein the culture does not comprise one or more hydrophobic carbon sources. In varying embodiments, the culture does not comprise one or more hydrophobic carbon sources selected from the group consisting of oils, alkanes, fatty acids, fatty esters and mixtures thereof. In varying embodiments, the yeast culture comprises a population of basidiomycetous yeast cells, one or more hydrophilic (e.g., non-hydrophobic) carbon sources, one or more hydrophobic carbons sources, and at least about 1 g/L glycolipid (e.g., sophorolipid), e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L glycolipid, e.g., up to about 450 g/L of glycolipid. In varying embodiments, total glycolipids are as measured after 1, 2, 3, 4, 5, 6, 7 or 8 days growth. In varying embodiments, the volume of the culture is at least about 5 L, 10 L, 25 L, 50 L, 75 L, 100 L, 250 L, 500 L, 1000 L, or more. In varying embodiments, the culture comprises less than about 2% (w/v) nitrogen, e.g., in the range of about 0.005% (w/v) to about 2% (w/v) nitrogen. In varying embodiments, the nitrogen source is selected from the group consisting of ammonia, ammonium salt, nitrate, nitrite, nucleotides, nucleosides, proteins, peptides, amino acids, urea and its derivatives, and mixtures thereof. In varying embodiments, the culture comprises about 0.05% (w/v) ammonium chloride. In varying embodiments, the culture comprises one or more hydrophilic carbon sources at a concentration in the range of about 0.2% (w/v) to about 70% (w/v), e.g., in the range of about 0.2% (w/v) to about 10%, 20%, 30%, 40%, 50% or 60% (w/v). In varying embodiments, the culture comprises a carbon to nitrogen ratio of about 5:1 to about 400:1, e.g., from about 10:1 to about 200:1, from about 20:1 to about 100:1, e.g., from about 25:1 to about 75:1, e.g., from about 30:1 to about 40:1, e.g., using a nitrogen source that can be consumed or utilized by the yeast cells. In varying embodiments, the hydrophilic carbon source is selected from the group consisting of monosaccharides, oligosaccharides, polysaccharides, sugar alcohols, polyols, organic acids, esters, aldehydes, ketones, alcohols, waste streams, plant materials, lignocellulosic hydrolysates, and mixtures thereof. In varying embodiments, the hydrophilic carbon source is a monosaccharide, an oligosaccharide or a polysaccharide and comprises one or more sugar moieties selected from the group consisting of glucose, sucrose, xylose, galactose, rhamnose, arabinose, mannose, cellobiose, galacturonic acid, lactose, sophorose, and mixtures thereof. In varying embodiments, the population of basidiomycetous yeast cells comprises cells in the taxonomic class Microbotryomycetes. In varying embodiments, the population of basidiomycetous yeast cells comprises cells in the taxonomic order Sporidiobolales. In varying embodiments, the population of basidiomycetous yeast cells comprises cells genera classified within the taxonomic order Sporidiobolales selected from the group consisting of *Rhodosporidiobolus* sp. (syn *Rhodosporidium* sp.), *Sporidiobolus*, *Rhodotorula*, and *Sporobolomyces*. In varying embodiments, the population of basidiomycetous yeast cells comprises *Rhodosporidiobolus* (syn *Rhodosporidium*) cells. In varying embodiments, the *Rhodosporidiobolus* (syn *Rhodosporidium*) cells are *Rhodotorula babjevae* (syn. *Rhodosporidium babjevae*) cells. In varying embodiments, the population of basidiomycetous yeast cells comprises one or more species selected from the group consisting of *Rhodotorula babjevae* (syn. *Rhodosporidium babjevae*), *Rhodotorula diobovata* (syn. *Rhodosporidium diobovatum*), *Rhodotorula kratochvilovae* (syn. *Rhodosporidium kratochvilovae*), *Rhodotorula paludigena* (syn. *Rhodosporidium paludigenum*), *Rhodotorula* aff. *paludigena* (syn. *Rhodosporidium* aff. *paludigenum*), *Rhodotorula sphaerocarpa* (syn. *Rhodosporidium sphaerocarpum*), *Rhodosporidiobolus* aff. *colostri* (syn. *Rhodotorula* aff. *colostri*), *Rhodotorula dairenensis*, *Rhodosporidiobolus ruineniae* (syn. *Sporidiobolus ruineniae*), and *Rhodosporidiobolus* aff. *nylandii* (syn. *Sporobolomyces* aff. *nylandii*). In varying embodiments, the population of basidiomycetous yeast cells comprises one or more strains selected from the group consisting of:

a) *Rhodotorula babjevae* (syn. *Rhodosporidium babjevae*) strain NRRL Y-67018 (UCDFST 04-877), b) *Rhodotorula babjevae* (syn. *Rhodosporidium babjevae*) strain NRRL Y-67017 (UCDFST 05-775), c) *Rhodotorula diobovata* (syn. *Rhodosporidium diobovatum*) strain NRRL Y-67015 (UCDFST 08-225), d) *Rhodotorula kratochvilovae* (syn. *Rhodosporidium kratochvilovae*) strain NRRL Y-67016 (UCDFST 05-632), e) *Rhodotorula paludigena* (syn. *Rhodosporidium paludigenum*) strain NRRL Y-67012 (UCDFST 09-163), f) *Rhodotorula* aff. *paludigena* (syn. *Rhodosporidium* aff. *paludigenum*) strain NRRL Y-67009 (UCDFST 81-84), g) *Rhodotorula sphaerocarpa* (syn. *Rhodosporidium sphaerocarpum*) strain NRRL Y-67010 (UCDFST 68-43), h) *Rhodosporidiobolus* aff. *colostri* (syn. *Rhodotorula* aff. *colostri*) strain NRRL Y-67014 (UCDFST 06-583), i) *Rhodotorula dairenensis* strain NRRL Y-67011 (UCDFST 68-257), j) *Rhodosporidiobolus* aff. *nylandii* (syn. *Sporobolomyces* aff. *nylandii*) strain NRRL Y-67013 (UCDFST 09-1303), and k) *Rhodosporidiobolus ruineniae* (syn. *Sporidiobolus ruineniae*) strain NRRL Y-17302 (UCDFST 67-67). In varying embodiments, cells do not comprise *Pseudohyphozyma bogoriensis*, (syn. *Rhodotorula bogoriensis*). In varying embodiments, the glycolipid comprises one or more sophorolipids. In varying embodiments, the glycolipid comprises a fatty acid comprising from 14 to 24 carbon atoms in length. In varying embodiments, the glycolipid sugar moiety or glycan is attached or bound to the omega or omega-1 carbon of the fatty acid. In varying embodiments, the glycolipid sugar moiety or glycan is attached or bound to a central carbon (e.g., not the alpha, omega or omega-1 carbon) of the fatty acid. In varying embodiments, the glycolipid sugar moiety or glycan is attached or bound to carbon that is not the alpha carbon (carboxyl carbon, C1) of the fatty acid. In varying embodiments, the glycolipid comprises a hydroxylated fatty acid. In varying embodiments, the glycolipid sugar moiety or glycan is non-acetylated, monoacetylated or diacetylated. In varying embodiments, the glycolipid sugar moiety or glycan comprises a disaccharide of glucose. In varying embodiments, the disaccharide of glucose comprises sophorose or cellobiose. In varying embodiments, the monoacetylated glycolipids comprise an acyl group on the 6' carbon or the 6" carbon of the disaccharide of glucose.

In varying embodiments of the yeast culture, the glycolipid comprises one or more glycolipids listed in Table 2.

In varying embodiments, the yeast culture comprises a glycolipid profile comprising:

i) at least about 15%, e.g., at least about 20%, 25%, 30%, 35%, 40%, up to about 45%, of a lactonic glycolipid (e.g., sophorolipid) with C18:2 fatty acid methylester or odd/branched chain length (Molecular Formula: $C_{31}H_{52}O_{12}$);

ii) at least about 5%, e.g., at least about 10%, 15%, 20%, up to about 25%, of a lactonic glycolipid (e.g., sophorolipid) with C20:0 fatty acid methylester or odd/branched chain length (Molecular Formula: $C_{33}H_{56}O_{12}$); and/or iii) at least about 5%, e.g., at least about 10%, 15%, up to about 20%, of a monoacetylated lactonic glycolipid (e.g., sophorolipid) with C20:1 fatty acid (Molecular Formula: $C_{34}H_{58}O_{13}$).

In varying embodiments, the yeast culture comprises a glycolipid profile comprising: at least about 25% of a lactonic glycolipid (e.g., sophorolipid) with C18:2 fatty acid methylester or odd/branched chain length (Molecular Formula: C31H52O12).

In varying embodiments, the yeast culture comprises a glycolipid profile comprising:

i) at least about 5%, e.g., at least about 6%, 7%, 8%, 9%, 10%, up to about 12%, of a lactonic glycolipid (e.g., sophorolipid) with C20:1 Fatty acid (Molecular Formula: C32H56O12);

ii) at least about 7%, e.g., at least about 8%, 9%, 10%, 11%, 12%, 13%, 14%, 15%, 16%, up to about 20%, of a monoacetylated lactonic glycolipid (e.g., sophorolipid) with C18:1 Fatty acid (Molecular Formula: C32H54O13);

iii) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

iv) at least about 15%, e.g., at least about 20%, 25%, 30%, 35%, 40%, 45%, up to 50%, of a lactonic glycolipid (e.g., sophorolipid) with C18:2 Fatty acid methylester (Molecular Formula: C31H52O12); and/or v) at least about 10%, e.g., at least about 15%, 20%, 25%, 30%, up to 35%, of a lactonic glycolipid (e.g., sophorolipid) with C20:0 Fatty acid methylester (Molecular Formula: C33H56O12). In some embodiments, the yeast culture further comprises:

vi) at least about 2%, e.g., at least about 3%, 4%, 5%, 6%, 7%, 8%, 9%, 10%, up to about 12%, of a diacetylated lactonic glycolipid (e.g., sophorolipid) with C18:1 Fatty acid (Molecular Formula: C34H56O14); and/or vii) at least about 1%, e.g., at least about 2%, 3%, 4%, 5%, 6%, 7%, 8%, 9%, 10%, up to about 12%, of a diacetylated lactonic glycolipid (e.g., sophorolipid) with C20:1 Fatty acid (Molecular Formula: C36H60O14).

In varying embodiments, the yeast culture comprises a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

ii) at least about 15%, e.g., at least about 20%, 25%, 30%, 35%, 40%, up to about 45%, of a diacetylated lactonic glycolipid (e.g., sophorolipid) with C18:1 Fatty acid (Molecular Formula: C34H56O14);

iii) at least about 10%, e.g., at least about 11%, 12%, 13%, 14%, 15%, 16%, 17%, 18%, 19%, 20%, up to about 25%, of a diacetylated lactonic glycolipid (e.g., sophorolipid) with C20:1 Fatty acid (Molecular Formula: C36H60O14);

iv) at least about 15%, e.g., at least about 20%, 25%, 30%, 35%, 40%, up to about 45%, of a lactonic glycolipid (e.g., sophorolipid) with C18:2 Fatty acid methylester (Molecular Formula: C31H52O12); and/or v) at least about 15%, e.g., at least about 20%, 25%, 30%, 35%, 40%, up to about 45%, of a lactonic glycolipid (e.g., sophorolipid) with C20:0 Fatty acid methylester (Molecular Formula: C33H56O12).

In varying embodiments, the yeast culture comprises a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

ii) at least about 25%, e.g., at least about 30%, 35%, 40%, 45%, up to 50%, of a diacetylated lactonic glycolipid (e.g., sophorolipid) with C18:1 Fatty acid (Molecular Formula: C34H56O14);

iii) at least about 15%, e.g., at least about 20%, 25%, 30%, 35%, 40%, 45%, up to 50%, of a diacetylated lactonic glycolipid (e.g., sophorolipid) with C20:1 Fatty acid (Molecular Formula: C36H60O14);

iv) at least about 5%, e.g., at least about 6%, 7%, 8%, 9%, 10%, up to about 12%, of a lactonic glycolipid (e.g., sophorolipid) with C18:2 Fatty acid methylester (Molecular Formula: C31H52O12); and/or v) at least about 15%, e.g., at least about 20%, 25%, 30%, 35%, 40%, up to about 45%, of a lactonic glycolipid (e.g., sophorolipid) with C20:0 Fatty acid methylester (Molecular Formula: C33H56O12).

In varying embodiments, the yeast culture comprises a glycolipid profile comprising:

i) at least about 5%, e.g., at least about 6%, 7%, 8%, 9%, 10%, up to about 12%, of a monoacetylated lactonic glycolipid (e.g., sophorolipid) with C20:1 Fatty acid (Molecular Formula: C34H58O13);

ii) at least about 10%, e.g., at least about 11%, 12%, 13%, 14%, 15%, 16%, 17%, 18%, 19%, 20%, up to about 25%, of a diacetylated lactonic glycolipid (e.g., sophorolipid) with C18:1 Fatty acid (Molecular Formula: C34H56O14);

iii) at least about 5%, e.g., at least about 6%, 7%, 8%, 9%, 10%, up to about 12%, of a diacetylated lactonic glycolipid (e.g., sophorolipid) with C20:1 Fatty acid (Molecular Formula: C36H60O14);

iv) at least about 15%, e.g., at least about 20%, 25%, 30%, 35%, 40%, up to about 45%, of a lactonic glycolipid (e.g., sophorolipid) with C18:2 Fatty acid methylester (Molecular Formula: C31H52O12); and/or v) at least about 40%, e.g., up to about 50%, of a lactonic glycolipid (e.g., sophorolipid) with C20:0 Fatty acid methylester (Molecular Formula: C33H56O12).

In varying embodiments, the yeast culture comprises a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C18:1 Fatty acid (Molecular Formula: C32H54O13);

ii) at least about 45% of a lactonic glycolipid (e.g., sophorolipid) with C18:2 Fatty acid methylester (Molecular Formula: C31H52O12); and/or iii) at least about 5%, e.g., at least about 6%, 7%, 8%, 9%, 10%, up to about 12%, of a lactonic glycolipid (e.g., sophorolipid) with C20:0 Fatty acid methylester (Molecular Formula: C33H56O12).

In varying embodiments, the one or more hydrophobic carbon sources are selected from the group consisting of oils, alkanes, fatty acids, fatty esters and mixtures thereof. In varying embodiments, the one or more glycolipids are present in the medium in a form that can be harvested without solvent extraction.

In a further aspect, provided are methods of producing one or more glycolipids. In some embodiments, the methods comprise culturing a population of basidiomycetous yeast cells in a yeast cell culture comprising one or more hydrophilic (e.g., non-hydrophobic) carbon sources, wherein the culture does not comprise one or more hydrophobic carbon sources, whereby the basidiomycetous yeast cells produce one or more glycolipids (e.g., sophorolipids). In some embodiments, the methods comprise culturing a population of basidiomycetous yeast cells in a yeast cell culture comprising one or more hydrophilic (e.g., non-hydrophobic) carbon sources and one or more hydrophobic carbon sources, whereby the basidiomycetous yeast cells produce one or more glycolipids (e.g., sophorolipids). In varying embodiments, additional hydrophilic carbon source is added, e.g., during any stage of growth including exponential growth, and after the population of basidiomycetous yeast cells reaches stationary phase. In varying embodiments, at least about 1 g/L glycolipid (e.g., sophorolipid), e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L glycolipid, e.g., up to about 450 g/L of glycolipid, is produced. In varying embodiments, total glycolipids are as measured after 1, 2, 3, 4, 5, 6, 7 or 8 days growth. In varying embodiments, the volume of the culture is at least about 5 L, 10 L, 25 L, 50 L, 75 L, 100 L, 250 L, 500 L, 1000 L, or more. In varying embodiments, the culture comprises less than about 2% (w/v) nitrogen, e.g., in the range of about 0.005% (w/v) to about 2% (w/v) nitrogen. In varying embodiments, the nitrogen source is selected from the group consisting of ammonia, ammonium salt, nitrate, nitrite, nucleotides, nucleosides, proteins, peptides, amino acids, urea and its derivatives, and mixtures thereof. In varying embodiments, the culture comprises about 0.05% (w/v) ammonium chloride. In varying embodiments, the culture comprises one or more hydrophilic carbon sources at a concentration in the range of about 0.2% (w/v) to about 70% (w/v), e.g., in the range of about 0.2% (w/v) to about 10%, 20%, 30%, 40%, 50% or 60% (w/v). In varying embodiments, the culture comprises a carbon to nitrogen ratio of about 5:1 to about 400:1, e.g., from about 10:1 to about 200:1, from about 20:1 to about 100:1, e.g., from about 25:1 to about 75:1, e.g., from about 30:1 to about 40:1, e.g., using a nitrogen source that can be consumed or utilized by the yeast cells. In varying embodiments, the hydrophilic carbon source is selected from the group consisting of monosaccharides, oligosaccharides, polysaccharides, sugar alcohols, polyols, organic acids, esters, aldehydes, ketones, alcohols, waste streams, plant materials, lignocellulosic hydrolysates, and mixtures thereof. In varying embodiments, the hydrophilic carbon source is a monosaccharide, an oligosaccharide or a polysaccharide and comprises one or more sugar moieties selected from the group consisting of glucose, sucrose, xylose, galactose, rhamnose, arabinose, mannose, cellobiose, galacturonic acid, lactose, sophorose, and mixtures thereof. In varying embodiments, the population of basidiomycetous yeast cells comprises cells in the taxonomic class Microbotryomycetes. In varying embodiments, the population of basidiomycetous yeast cells comprises cells in the taxonomic order Sporidiobolales. In varying embodiments, the population of basidiomycetous yeast cells comprises genera classified within the taxonomic order Sporidiobolales selected from the group consisting of *Rhodosporidium* sp., *Sporidiobolus*, *Rhodotorula*, and *Sporobolomyces*. In varying embodiments, the population of basidiomycetous yeast cells comprises *Rhodosporidium* cells. In varying embodiments, the *Rhodosporidium* cells are *Rhodotorula babjevae* (syn. *Rhodosporidium babjevae*) cells. In varying embodiments, the population of basidiomycetous yeast cells comprises one or more species selected from the group consisting of *Rhodotorula babjevae* (syn. *Rhodosporidium babjevae*), *Rhodotorula diobovata* (syn. *Rhodosporidium diobovatum*), *Rhodotorula kratochvilovae* (syn. *Rhodosporidium kratochvilovae*), *Rhodotorula paludigena* (syn. *Rhodosporidium paludigenum*), *Rhodotorula* aff. *paludigena* (syn. *Rhodosporidium* aff. *paludigenum*), *Rhodotorula sphaerocarpa* (syn. *Rhodosporidium sphaerocarpum*), *Rhodosporidiobolus* aff. *colostri* (syn. *Rhodotorula* aff. *colostri*), *Rhodotorula dairenensis*, *Rhodosporidiobolus ruineniae* (syn. *Sporidiobolus ruineniae*), and *Rhodosporidiobolus* aff. *nylandii* (syn. *Sporobolomyces* aff. *nylandii*). In varying embodiments, the population of basidiomycetous yeast cells comprises one or more strains selected from the group consisting of:

a) *Rhodotorula babjevae* (syn. *Rhodosporidium babjevae*) strain NRRL Y-67018 (UCDFST 04-877), b) *Rhodotorula babjevae* (syn. *Rhodosporidium babjevae*) strain NRRL Y-67017 (UCDFST 05-775), c) *Rhodotorula diobovata* (syn. *Rhodosporidium diobovatum*) strain NRRL Y-67015 (UCDFST 08-225), d) *Rhodotorula kratochvilovae* (syn. *Rhodosporidium kratochvilovae*) strain NRRL Y-67016 (UCDFST 05-632), e) *Rhodotorula paludigena* (syn. *Rhodosporidium paludigenum*) strain NRRL Y-67012 (UCDFST 09-163), f) *Rhodotorula* aff. *paludigena* (syn. *Rhodosporidium* aff. *paludigenum*) strain NRRL Y-67009 (UCDFST 81-84), g) *Rhodotorula sphaerocarpa* (syn. *Rhodosporidium sphaerocarpum*) strain NRRL Y-67010 (UCDFST 68-43), h) *Rhodosporidiobolus* aff. *colostri* (syn. *Rhodotorula* aff. *colostri*) strain NRRL Y-67014 (UCDFST 06-583), i) *Rhodotorula dairenensis* strain NRRL Y-67011 (UCDFST 68-257), j) *Rhodosporidiobolus* aff. *nylandii* (syn. *Sporobolomyces* aff. *nylandii*) strain NRRL Y-67013 (UCDFST 09-1303), and k) *Rhodosporidiobolus ruineniae* (syn. *Sporidiobolus ruineniae*) strain NRRL Y-17302 (UCDFST 67-67). In varying embodiments, the cells do not comprise *Pseudohyphozyma bogoriensis*, (syn. *Rhodotorula bogoriensis*). In varying embodiments, the glycolipid comprises one or more sophorolipids. In varying embodiments, the glycolipid comprises a fatty acid comprising from 14 to 24 carbon atoms in length. In varying embodiments, the glycolipid sugar moiety or glycan is attached or bound to the omega or omega-1 carbon of the fatty acid. In varying embodiments, the glycolipid sugar moiety or glycan is attached or bound to a central carbon (e.g., not the alpha, omega or omega-1 carbon) of the fatty acid. In varying embodiments, the glycolipid sugar moiety or glycan is attached or bound to carbon that is not the alpha carbon (carboxyl carbon, C1) of the fatty acid. In varying embodiments, the glycolipid comprises a hydroxylated fatty acid. In varying embodiments, the glycolipid sugar moiety or glycan is non-acetylated, monoacetylated or diacetylated. In varying embodiments, the glycolipid sugar moiety or glycan comprises a disaccharide of glucose. In varying embodiments, the disaccharide of glucose comprises sophorose or cellobiose. In varying embodiments, the monoacetylated glycolipids comprise an acyl group on the 6' carbon or the 6" carbon of the disaccharide of glucose. In varying embodiments of the yeast culture, the glycolipid comprises one or more glycolipids listed in Table 2.

In varying embodiments of the methods of producing, the yeast culture comprises a glycolipid profile comprising:

i) at least about 15%, e.g., at least about 20%, 25%, 30%, 35%, 40%, up to about 45%, of a lactonic glycolipid (e.g., sophorolipid) with C18:2 fatty acid methylester or odd/branched chain length (Molecular Formula: $C_{31}H_{52}O_{12}$);

ii) at least about 5%, e.g., at least about 10%, 15%, 20%, up to about 25%, of a lactonic glycolipid (e.g., sophorolipid) with C20:0 fatty acid methylester or odd/branched chain length (Molecular Formula: $C_{33}H_{56}O_{12}$); and/or iii) at least about 5%, e.g., at least about 10%, 15%, up to about 20%, of a monoacetylated lactonic glycolipid (e.g., sophorolipid) with C20:1 fatty acid (Molecular Formula: $C_{34}H_{58}O_{13}$).

In varying embodiments of the methods of producing, the yeast culture comprises a glycolipid profile comprising: at least about 25% of a lactonic glycolipid (e.g., sophorolipid) with C18:2 fatty acid methylester or odd/branched chain length (Molecular Formula: C31H52O12).

In varying embodiments of the methods of producing, the yeast culture comprises a glycolipid profile comprising:

i) at least about 5%, e.g., at least about 6%, 7%, 8%, 9%, 10%, up to about 12%, of a lactonic glycolipid (e.g., sophorolipid) with C20:1 Fatty acid (Molecular Formula: C32H56O12);

ii) at least about 7%, e.g., at least about 8%, 9%, 10%, 11%, 12%, 13%, 14%, 15%, 16%, up to about 20%, of a monoacetylated lactonic glycolipid (e.g., sophorolipid) with C18:1 Fatty acid (Molecular Formula: C32H54O13);

iii) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

iv) at least about 15%, e.g., at least about 20%, 25%, 30%, 35%, 40%, 45%, up to 50%, of a lactonic glycolipid (e.g., sophorolipid) with C18:2 Fatty acid methylester (Molecular Formula: C31H52O12); and/or v) at least about 10%, e.g., at least about 15%, 20%, 25%, 30%, up to 35%, of a lactonic glycolipid (e.g., sophorolipid) with C20:0 Fatty acid methylester (Molecular Formula: C33H56O12). In some embodiments, the yeast culture further comprises:

vi) at least about 2%, e.g., at least about 3%, 4%, 5%, 6%, 7%, 8%, 9%, 10%, up to about 12%, of a diacetylated lactonic glycolipid (e.g., sophorolipid) with C18:1 Fatty acid (Molecular Formula: C34H56O14); and/or vii) at least about 1%, e.g., at least about 2%, 3%, 4%, 5%, 6%, 7%, 8%, 9%, 10%, up to about 12%, of a diacetylated lactonic glycolipid (e.g., sophorolipid) with C20:1 Fatty acid (Molecular Formula: C36H60O14).

In varying embodiments of the methods of producing, the yeast culture comprises a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

ii) at least about 15%, e.g., at least about 20%, 25%, 30%, 35%, 40%, up to about 45%, of a diacetylated lactonic glycolipid (e.g., sophorolipid) with C18:1 Fatty acid (Molecular Formula: C34H56O14);

iii) at least about 10%, e.g., at least about 11%, 12%, 13%, 14%, 15%, 16%, 17%, 18%, 19%, 20%, up to about 25%, of a diacetylated lactonic glycolipid (e.g., sophorolipid) with C20:1 Fatty acid (Molecular Formula: C36H60O14);

iv) at least about 15%, e.g., at least about 20%, 25%, 30%, 35%, 40%, up to about 45%, of a lactonic glycolipid with C18:2 Fatty acid methylester (Molecular Formula: C31H52O12); and/or v) at least about 15%, e.g., at least about 20%, 25%, 30%, 35%, 40%, up to about 45%, of a lactonic glycolipid (e.g., sophorolipid) with C20:0 Fatty acid methylester (Molecular Formula: C33H56O12).

In varying embodiments of the methods of producing, the yeast culture comprises a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

ii) at least about 25%, e.g., at least about 30%, 35%, 40%, 45%, up to 50%, of a diacetylated lactonic glycolipid (e.g., sophorolipid) with C18:1 Fatty acid (Molecular Formula: C34H56O14);

iii) at least about 15%, e.g., at least about 20%, 25%, 30%, 35%, 40%, 45%, up to 50%, of a diacetylated lactonic glycolipid (e.g., sophorolipid) with C20:1 Fatty acid (Molecular Formula: C36H60O14);

iv) at least about 5%, e.g., at least about 6%, 7%, 8%, 9%, 10%, up to about 12%, of a lactonic glycolipid (e.g., sophorolipid) with C18:2 Fatty acid methylester (Molecular Formula: C31H52O12); and/or v) at least about 15%, e.g., at least about 20%, 25%, 30%, 35%, 40%, up to about 45%, of a lactonic glycolipid (e.g., sophorolipid) with C20:0 Fatty acid methylester (Molecular Formula: C33H56O12).

In varying embodiments of the methods of producing, the yeast culture comprises a glycolipid profile comprising:

i) at least about 5%, e.g., at least about 6%, 7%, 8%, 9%, 10%, up to about 12%, of a monoacetylated lactonic glycolipid (e.g., sophorolipid) with C20:1 Fatty acid (Molecular Formula: C34H58O13);

ii) at least about 10%, e.g., at least about 11%, 12%, 13%, 14%, 15%, 16%, 17%, 18%, 19%, 20%, up to about 25%, of a diacetylated lactonic glycolipid (e.g., sophorolipid) with C18:1 Fatty acid (Molecular Formula: C34H56O14);

iii) at least about 5%, e.g., at least about 6%, 7%, 8%, 9%, 10%, up to about 12%, of a diacetylated lactonic glycolipid (e.g., sophorolipid) with C20:1 Fatty acid (Molecular Formula: C36H60O14);

iv) at least about 15%, e.g., at least about 20%, 25%, 30%, 35%, 40%, up to about 45%, of a lactonic glycolipid (e.g., sophorolipid) with C18:2 Fatty acid methylester (Molecular Formula: C31H52O12); and/or v) at least about 40%, e.g., up to about 50%, of a lactonic glycolipid (e.g., sophorolipid) with C20:0 Fatty acid methylester (Molecular Formula: C33H56O12).

In varying embodiments of the methods of producing, the yeast culture comprises a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C18:1 Fatty acid (Molecular Formula: C32H54O13);

ii) at least about 45% of a lactonic glycolipid (e.g., sophorolipid) with C18:2 Fatty acid methylester (Molecular Formula: C31H52O12); and/or iii) at least about 5%, e.g., at least about 6%, 7%, 8%, 9%, 10%, up to about 12%, of a lactonic glycolipid (e.g., sophorolipid) with C20:0 Fatty acid methylester (Molecular Formula: C33H56O12).

In varying embodiments of the methods of producing, the one or more hydrophobic carbon sources are selected from the group consisting of oils, alkanes, fatty acids, fatty esters and mixtures thereof. In varying embodiments, the methods further comprise purifying and/or isolating the glycolipid. In varying embodiments, the glycolipid does not need to be purified from a hydrophobic carbon source. In varying embodiments, the glycolipid can be purified and/or isolated without cell lysis. In some embodiments, the yeast cells secrete the one or more glycolipids into the medium in a form that can be harvested without solvent extraction.

In a related aspect, provided are glycolipid compositions produced according to the methods described above and herein. In another aspect, provided are compositions comprising one or more glycolipids listed in Table 2. In varying embodiments, the glycolipid compositions are selected from the group consisting of a cleanser, a detergent, a surfactant (e.g., for recovery of oil), a wetting agent, an antifoam agent, an emulsifier, an emollient, a dispersant (e.g., for cleanup of oil including spilled petroleum), a humectant, an antibacterial agent, an antiviral agent, an antifungal agent, a spermicide, an insecticide, a lubricant, an adhesive, a crystal modifier, an instantizer, a viscosity modifier, a mixing/blending aid, a release agent, a cream, a foam, a mousse, a lotion, a balm, an ointment, and an oleochemical composition. In varying embodiments, glycolipid composition is free of any hydrophobic carbon source. In varying embodiments, the method is performed as a batch, fed batch or continuous-feed process.

In varying embodiments, the compositions comprise a glycolipid profile comprising:

i) at least about 15%, e.g., at least about 20%, 25%, 30%, 35%, 40%, up to about 45%, of a lactonic glycolipid (e.g., sophorolipid) with C18:2 fatty acid methylester or odd/branched chain length (Molecular Formula: C31H52O12);

ii) at least about 5%, e.g., at least about 10%, 15%, 20%, up to about 25%, of a lactonic glycolipid (e.g., sophorolipid) with C20:0 fatty acid methylester or odd/branched chain length (Molecular Formula: C33H56O12); and/or iii) at least about 5%, e.g., at least about 10%, 15%, up to about 20%, of a monoacetylated lactonic glycolipid (e.g., sophorolipid) with C20:1 fatty acid (Molecular Formula: C34H58O13).

In varying embodiments, the compositions comprise a glycolipid profile comprising at least about 25% of a lactonic glycolipid (e.g., sophorolipid) with C18:2 fatty acid methylester or odd/branched chain length (Molecular Formula: C31H52O12).

In varying embodiments, the compositions comprise a glycolipid profile comprising:

i) at least about 5%, e.g., at least about 6%, 7%, 8%, 9%, 10%, up to about 12%, of a lactonic glycolipid (e.g., sophorolipid) with C20:1 Fatty acid (Molecular Formula: C32H56O12);

ii) at least about 7%, e.g., at least about 8%, 9%, 10%, 11%, 12%, 13%, 14%, 15%, 16%, up to about 20%, of a monoacetylated lactonic glycolipid (e.g., sophorolipid) with C18:1 Fatty acid (Molecular Formula: C32H54O13);

iii) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

iv) at least about 15%, e.g., at least about 20%, 25%, 30%, 35%, 40%, 45%, up to 50%, of a lactonic glycolipid (e.g., sophorolipid) with C18:2 Fatty acid methylester (Molecular Formula: C31H52O12); and/or v) at least about 10%, e.g., at least about 15%, 20%, 25%, 30%, up to 35%, of a lactonic glycolipid (e.g., sophorolipid) with C20:0 Fatty acid methylester (Molecular Formula: C33H56O12). In some embodiments, the yeast culture further comprises:

vi) at least about 2%, e.g., at least about 3%, 4%, 5%, 6%, 7%, 8%, 9%, 10%, up to about 12%, of a diacetylated lactonic glycolipid (e.g., sophorolipid) with C18:1 Fatty acid (Molecular Formula: C34H56O14); and/or vii) at least about 1%, e.g., at least about 2%, 3%, 4%, 5%, 6%, 7%, 8%, 9%, 10%, up to about 12%, of a diacetylated lactonic glycolipid (e.g., sophorolipid) with C20:1 Fatty acid (Molecular Formula: C36H60O14).

In varying embodiments, the compositions comprise a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

ii) at least about 15%, e.g., at least about 20%, 25%, 30%, 35%, 40%, up to about 45%, of a diacetylated lactonic glycolipid (e.g., sophorolipid) with C18:1 Fatty acid (Molecular Formula: C34H56O14);

iii) at least about 10%, e.g., at least about 11%, 12%, 13%, 14%, 15%, 16%, 17%, 18%, 19%, 20%, up to about 25%, of a diacetylated lactonic glycolipid (e.g., sophorolipid) with C20:1 Fatty acid (Molecular Formula: C36H60O14);

iv) at least about 15%, e.g., at least about 20%, 25%, 30%, 35%, 40%, up to about 45%, of a lactonic glycolipid (e.g., sophorolipid) with C18:2 Fatty acid methylester (Molecular Formula: C31H52O12); and/or v) at least about 15%, e.g., at least about 20%, 25%, 30%, 35%, 40%, up to about 45%, of a lactonic glycolipid (e.g., sophorolipid) with C20:0 Fatty acid methylester (Molecular Formula: C33H56O12).

In varying embodiments, the compositions comprise a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C20:1 Fatty acid (Molecular Formula: C34H58O13);

ii) at least about 25%, e.g., at least about 30%, 35%, 40%, 45%, up to 50%, of a diacetylated lactonic glycolipid (e.g., sophorolipid) with C18:1 Fatty acid (Molecular Formula: C34H56O14);

iii) at least about 15%, e.g., at least about 20%, 25%, 30%, 35%, 40%, 45%, up to 50%, of a diacetylated lactonic glycolipid (e.g., sophorolipid) with C20:1 Fatty acid (Molecular Formula: C36H60O14);

iv) at least about 5%, e.g., at least about 6%, 7%, 8%, 9%, 10%, up to about 12%, of a lactonic glycolipid (e.g., sophorolipid) with C18:2 Fatty acid methylester (Molecular Formula: C31H52O12); and/or v) at least about 15%, e.g., at least about 20%, 25%, 30%, 35%, 40%, up to about 45%, of a lactonic glycolipid (e.g., sophorolipid) with C20:0 Fatty acid methylester (Molecular Formula: C33H56O12).

In varying embodiments, the compositions comprise a glycolipid profile comprising:

i) at least about 5%, e.g., at least about 6%, 7%, 8%, 9%, 10%, up to about 12%, of a monoacetylated lactonic glycolipid (e.g., sophorolipid) with C20:1 Fatty acid (Molecular Formula: C34H58O13);

ii) at least about 10%, e.g., at least about 11%, 12%, 13%, 14%, 15%, 16%, 17%, 18%, 19%, 20%, up to about 25%, of a diacetylated lactonic glycolipid (e.g., sophorolipid) with C18:1 Fatty acid (Molecular Formula: C34H56O14);

iii) at least about 5%, e.g., at least about 6%, 7%, 8%, 9%, 10%, up to about 12%, of a diacetylated lactonic glycolipid (e.g., sophorolipid) with C20:1 Fatty acid (Molecular Formula: C36H60O14);

iv) at least about 15%, e.g., at least about 20%, 25%, 30%, 35%, 40%, up to about 45%, of a lactonic glycolipid (e.g., sophorolipid) with C18:2 Fatty acid methylester (Molecular Formula: C31H52O12); and/or v) at least about 40%, e.g., up to about 50%, of a lactonic glycolipid (e.g., sophorolipid) with C20:0 Fatty acid methylester (Molecular Formula: C33H56O12).

In varying embodiments, the compositions comprise a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid (e.g., sophorolipid) with C18:1 Fatty acid (Molecular Formula: C32H54O13);

ii) at least about 45% of a lactonic glycolipid (e.g., sophorolipid) with C18:2 Fatty acid methylester (Molecular Formula: C31H52O12); and/or iii) at least about 5%, e.g., at least about 6%, 7%, 8%, 9%, 10%, up to about 12%, of a lactonic glycolipid (e.g., sophorolipid) with C20:0 Fatty acid methylester (Molecular Formula: C33H56O12).

In a further aspect, provided is a yeast cell of a yeast strain selected from the group consisting of:

a) *Rhodotorula babjevae* (syn. *Rhodosporidium babjevae*) strain NRRL Y-67018 (UCDFST 04-877),
b) *Rhodotorula babjevae* (syn. *Rhodosporidium babjevae*) strain NRRL Y-67017 (UCDFST 05-775),
c) *Rhodotorula diobovata* (syn. *Rhodosporidium diobovatum*) strain NRRL Y-67015 (UCDFST 08-225),
d) *Rhodotorula kratochvilovae* (syn. *Rhodosporidium kratochvilovae*) strain NRRL Y-67016 (UCDFST 05-632),
e) *Rhodotorula paludigena* (syn. *Rhodosporidium paludigenum*) strain NRRL Y-67012 (UCDFST 09-163),
f) *Rhodotorula* aff. *paludigena* (syn. *Rhodosporidium* aff. *paludigenum*) strain NRRL Y-67009 (UCDFST 81-84),
g) *Rhodotorula sphaerocarpa* (syn. *Rhodosporidium sphaerocarpum*) strain NRRL Y-67010 (UCDFST 68-43),
h) *Rhodosporidiobolus* aff. *colostri* (syn. *Rhodotorula* aff. *colostri*) strain NRRL Y-67014 (UCDFST 06-583),
i) *Rhodotorula dairenensis* strain NRRL Y-67011 (UCDFST 68-257), and
j) *Rhodosporidiobolus* aff. *nylandii* (syn. *Sporobolomyces* aff. *nylandii*) strain NRRL Y-67013 (UCDFST 09-1303).

Further provided is a population of yeast cells comprising one or more yeast strains as described above and herein. Further provided is a yeast culture comprising one or more yeast strains as described above and herein.

Definitions

The term "population of yeast cells" refers to two or more yeast cells.

The term "hydrophobic carbon source" refers to an organic compound that is insoluble in water or has a solubility in water of less than 1 g/L.

The term "hydrophilic carbon source refers to an organic compound that is soluble in water at concentrations greater than 1 g/L.

DETAILED DESCRIPTION

1. Introduction

Figure 1:
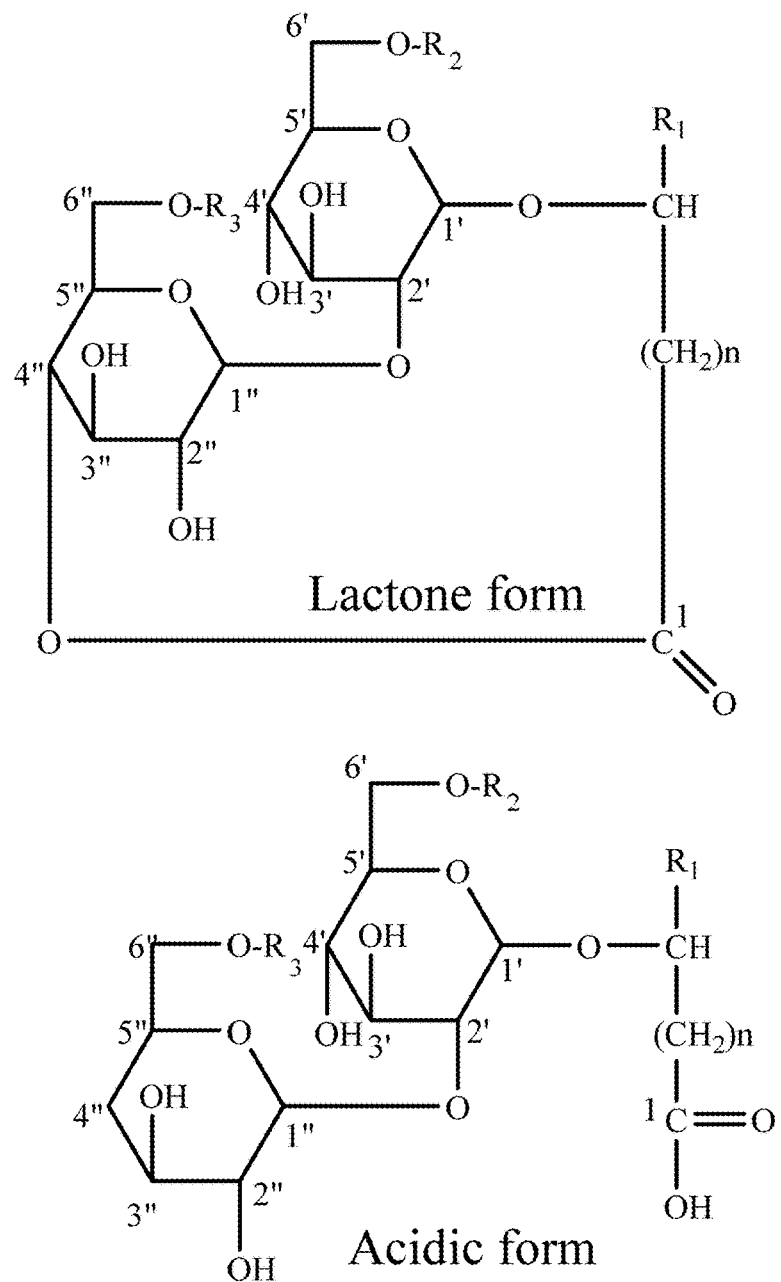
FIG. 1 illustrates the generic chemical structures for acidic and lactonic glycolipids. In *S. bombicola*, $R_1$=$CH_3$ or H; n is predominantly 15 or 16, as the disaccharide is attached to the ω or the ω−1 carbon of the fatty acid, and the fatty acid backbone comprises typically 18 carbons. In *Pseudohyphozyma bogoriensis*, (syn. *R. bogoriensis*), $R_1$ is predominantly $(CH_2)8$ $CH_3$ and n is predominantly 11, as the disaccharide is attached to carbon thirteen in the middle of the fatty acid. $R_2$ & $R_3$=$COCH_3$ or H.

Methods, yeast cultures and glycolipid compositions are described herein, based in part on the discovery of yeast species that convert hydrophilic carbon sources (e.g., simple sugars) into lipids, and then secrete them into the medium in a form that can be harvested without solvent extraction—a breakthrough that addresses obstacles of harvesting and extraction, described above.

The methods, yeast cultures and glycolipid compositions described herein enable development of yeast-based processes to convert lignocellulosic hydrolysates into a suite of products, including easily harvested lipids, e.g., for use in the sustainable production of biodiesel and other oleochemicals.

The methods, yeast cultures and glycolipid compositions described herein overcome the disadvantages of the prior art in that glycolipids are produced by these yeasts in commercially relevant quantities without provision of hydrophobic substrate or substrates. The methods, yeast cultures and glycolipid compositions described herein entail the use of yeasts in phylum Basidiomycota, class Microbotryomycetes, order Sporidiobolales, genera *Rhodotorula*, *Rhodosporidium*, *Sporidiobolus* and *Sporobolomyces* for conversion of glucose or other carbohydrates to glycolipids (Note that *Pseudohyphozyma bogoriensis*, (syn. *Rhodotorula bogoriensis*), and several other *Rhodotorula* species, are members of other taxonomic orders and classes because *Rhodotorula* is a polyphyletic genus. Herein, we describe the use of *Rhodotorula* species that are in the order Sporidiobolales.). Glycolipids are produced by these yeasts in commercially relevant quantities without provision of hydrophobic substrate or substrates. The glycolipids that are produced are similar to but structurally distinct from those produced by *Starmerella* and related ascomycetous yeasts, and structurally distinct from glycolipids produced by *Pseudohyphozyma bogoriensis*, (syn. *Rhodotorula bogoriensis*).

Yeasts have been used as model organisms for decades. The first eukaryotic genome to be sequenced was that of the yeast *Saccharomyces cerevisiae* [26], in part due to its long history of use as a model organism for genetics research, and for food, beverage and biofuel production. *Starmerella bombicola* is a model yeast for conversion of carbohydrate plus fatty acid to secreted glycolipids [18, 27, 28].

We identified basidiomycetous yeast strains that are able to secrete glycolipids. In addition to producing between 0.7 and 12 g/L intracellular lipids, primarily triacylglycerols (TAGs), these yeasts are able to secrete up to an estimated 10-12 g/L crude glycolipids.

Basidiomycetous yeasts in the order Sporidiobolales are able to directly convert less expensive simple sugars into significant quantities of secreted glycolipids, opening up opportunities to use these glycolipids for a broader range of consumer and industrial surfactant applications. The present yeast cultures, methods and glycolipid compositions facilitate the development of an economically favorable industrial process for biosurfactant production.

The advantages of these basidiomycetous yeasts for production of glycolipids include without limitation:

While ascomycete yeasts such as *Starmerella bombicola* currently used to produce SLs must be fed both glucose and a lipid substrates (e.g., hydrophobic carbon sources) [5,17], these basidiomycetous yeast produce and secrete significant quantities of SL when fed only hydrophilic carbon sources (e.g., simple sugars such as glucose, xylose or sucrose).

The oils are secreted, so cell harvesting and lysis are not necessary.

The oils are heavier than water and yeast cells, so inexpensive gravimetric techniques can be used to harvest them.

The oils are extracellular and insoluble in water, so organic solvent extraction is not required. This greatly reduces both facility construction and processing costs, decreases environmental impact and increases operational safety.

Because the cells producing the SLs need not be harvested or lysed, a continuous or fed-batch culture system further reduces costs.

2. Methods of Producing Glycolipids

Generally, the methods entail culturing a population of basidiomycetous yeast cells in a yeast culture containing relatively high concentrations of a hydrophilic (e.g., non-hydrophobic) carbon source and low concentrations of nitrogen, and with or without the presence of a hydrophobic carbon source.

a. Yeast Cultures

Provided are yeast cultures for producing one or more glycolipids according to the methods described herein. In varying embodiments, the yeast culture comprises a population of basidiomycetous yeast cells, a hydrophilic (e.g., non-hydrophobic) carbon source, and at least about 1 g/L total glycolipid, e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L total glycolipid, e.g., up to about 450 g/L of total glycolipid, wherein the culture does not comprise one or more hydrophobic carbon sources. The one or more glycolipids are extracellularly secreted by the yeast cells into the media and can be harvested without cell lysis and extracted without use of organic solvent.

In varying embodiments, the culture does not comprise one or more hydrophobic carbon sources. In varying embodiments, the culture comprises one or more hydrophobic carbon sources. In varying embodiments, the one or more hydrophobic carbon sources are selected from the group consisting of oils, hydrocarbons, unsaturated hydrocarbons, fatty acids, fatty esters including glycerides and mixtures thereof, alcohols, diols, sterols, waste streams, hydrolysates, and mixtures thereof. In varying embodiments, the one or more hydrophobic carbon sources include an oil, e.g., a mineral oil, animal oil, a plant oil, a microbial oil (e.g., an algal oil, a yeast oil, a bacterial oil), a fish oil, a vegetable oil or a nutseed oil, e.g., canola oil, rapeseed oil, olive oil, almond oil, walnut oil, peanut oil, coconut oil, or others, or mixtures thereof. In varying embodiments, the one or more hydrophobic carbon sources comprise at least 8 carbon atoms, e.g., an alkane, fatty acid, fatty ester, alcohol, diol comprising 8 or more carbon atoms, e.g., from 8 to 24 carbon atoms. In varying embodiments, the one or more hydrophobic carbon sources are selected from a primary or secondary alcohol or diol having from about 4 to about 24 carbon atoms, e.g., having 8 or more carbon atoms, e.g., from 8 to 24 carbon atoms or from 8 to 14 carbon atoms. In varying embodiments, the one or more hydrophobic carbon sources are selected from an aliphatic linear or branched hydrocarbon, which may contain one or more substituents selected from the group consisting of —OR, —COOH, and an ester with a carbon chain length of about 4 to about 24 carbon atoms, e.g., having 8 or more carbon atoms, e.g., from 8 to 24 carbon atoms or from 8 to 14 carbon atoms.

In varying embodiments, the culture comprises less than about 2% (w/v) nitrogen, e.g., in the range of about 0.005% (w/v) to about 2% (w/v) nitrogen. In varying embodiments, the nitrogen source is selected from the group consisting of ammonia, ammonium salt, nitrate, nitrite, nucleotides, nucleosides, proteins, peptides, amino acids, urea and its derivatives, and mixtures thereof. In varying embodiments, the culture comprises about 0.05% (w/v) ammonium chloride.

In varying embodiments, the culture comprises one or more hydrophilic carbon sources at a concentration of at least about 0.2% (w/v), e.g., in the range of about 0.2% (w/v) to about 70% (w/v), e.g., in the range of about 0.2% (w/v) to about 10%, 20%, 30%, 40%, 50% or 60% (w/v). In varying embodiments, the culture comprises a carbon to nitrogen ratio of about 5:1 to about 400:1, e.g., from about 10:1 to about 200:1, from about 20:1 to about 100:1, e.g., from about 25:1 to about 75:1, e.g., from about 30:1 to about 40:1, e.g., using a nitrogen source that can be consumed or utilized by the yeast cells.

In varying embodiments, the hydrophilic carbon source is selected from the group consisting of monosaccharides, oligosaccharides, polysaccharides, sugar alcohols, polyols, organic acids, esters, aldehydes, ketones, alcohols, waste streams, plant materials, lignocellulosic hydrolysates, and mixtures thereof. In varying embodiments, the hydrophilic carbon source is a monosaccharide, a disaccharide, an oligosaccharide or a polysaccharide and comprises one or more sugars selected from the group consisting of glucose, sucrose, xylose, galactose, rhamnose, arabinose, mannose, cellobiose, galacturonic acid, lactose, sophorose, and mixtures thereof.

In varying embodiments, the population of basidiomycetous yeast cells in the yeast culture comprises basidiomycetous yeast cells within the taxonomic class Microbotryomycetes. In varying embodiments, the population of basidiomycetous yeast cells comprises cells within the taxonomic order Sporidiobolales. In varying embodiments, the basidiomycetous yeast cells are within the *Rhodotorula glutinis* clade. In varying embodiments, the population of basidiomycetous yeast cells comprises genera classified within the taxonomic order Sporidiobolales selected from the group consisting of *Rhodosporidium* sp., *Sporidiobolus*, *Rhodotorula*, and *Sporobolomyces*. In varying embodiments, the population of basidiomycetous yeast cells comprises *Rhodosporidium* cells. In varying embodiments, the *Rhodosporidium* cells are *Rhodotorula babjevae* (syn. *Rhodosporidium babjevae*) cells. In varying embodiments, the population of basidiomycetous yeast cells comprises species selected from the group consisting of *Rhodotorula babjevae* (syn. *Rhodosporidium babjevae*), *Rhodotorula diobovata* (syn. *Rhodosporidium diobovatum*), *Rhodotorula kratochvilovae* (syn. *Rhodosporidium kratochvilovae*), *Rhodotorula paludigena* (syn. *Rhodosporidium paludigenum*), *Rhodotorula* aff. *paludigena* (syn. *Rhodosporidium* aff. *paludigenum*), *Rhodotorula sphaerocarpa* (syn. *Rhodosporidium sphaerocarpum*), *Rhodosporidiobolus* aff. *colostri*

(syn. *Rhodotorula* aff. *colostri*), *Rhodotorula dairenensis*, *Rhodosporidiobolus ruineniae* (syn. *Sporidiobolus ruineniae*), and *Rhodosporidiobolus* aff. *nylandii* (syn. *Sporobolomyces* aff. *nylandii*). In varying embodiments, the cells do not comprise *Pseudohyphozyma bogoriensis*, (syn. *Rhodotorula bogoriensis*), a species in class Microbotryomycetes but not in order Sporidiobolales [29].

In varying embodiments, the yeast culture comprises hydrophilic carbon source (e.g., a mono- or di-saccharide, e.g., glucose) (30 g/L), yeast extract (1.5 g/L), ammonium chloride (0.5 g/L), potassium phosphate monobasic (7.0 g/L), sodium phosphate dibasic (5.0 g/L), magnesium sulfate hexahydrate (1.5 g/L) and micronutrient solution comprised of various salts (10 mL/L). In varying embodiments, the yeast culture is supplemented with extra hydrophilic carbon source (e.g., a mono- or di-saccharide, e.g., glucose) to a concentration of at least about 50 g/L, e.g., at least about 75 g/L, 100 g/L, 125 g/L, 150 g/L, 175 g/L, 200 g/L, 225 g/L, 250 g/L, 275 g/L or 300 g/L.

b. Methods of Producing Glycolipids

Provided are methods of producing one or more glycolipids, comprising culturing a population of basidiomycetous yeast cells in a yeast cell culture comprising a hydrophilic carbon source, wherein the culture does not comprise one or more hydrophobic carbon sources, whereby the basidiomycetous yeast cells produce and secrete one or more glycolipids. As discussed above, the yeast cells are grown in a yeast cell culture media having a high carbon to nitrogen (C/N) ratio. In varying embodiments, the hydrophilic carbon source (e.g., a mono- or di-saccharide, e.g., glucose) is added after the population of basidiomycetous yeast cells reaches stationary phase. Embodiments of the yeast culture are as described above. When culturing yeast cells in the herein described yeast cultures and according to the methods described herein, at least about at least about 1 g/L glycolipid, e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L glycolipid, e.g., up to about 450 g/L of glycolipid, are secreted into the yeast culture medium.

The population of basidiomycetous yeast cells is cultured in the yeast cell culture medium under conditions sufficient for yeast cell growth and glycolipid production and secretion. The embodiments of illustrative yeast cultures are as described above and herein. For example, in certain embodiments, the yeast cells are cultured at a temperature of about 24° C. with continuous agitation (e.g., in shake flasks, e.g., baffled shake flasks, e.g., at about 200 rpm) for time period sufficient for yeast cell growth and glycolipid production and secretion, e.g., for about 6 hours to about 96 hours post inoculation with yeast cells, e.g., about 6, 12, 24, 48, 72 or 96 hours post inoculation with yeast cells. The yeast cells are further provided with a sufficient amount of a hydrophilic carbon source, e.g., as described above. In varying embodiments, total glycolipids are measured and determined after 1, 2, 3, 4, 5, 6, 7 or 8 days growth.

During and after growth in shake flasks, a hydrophobic liquid settles to the bottom of the growth flask. In varying embodiments, the one or more glycolipids secreted by the yeast cells has density in the range of about 1.00 g/mL to about 1.10 g/mL, e.g., from about 1.08 g/mL to about 1.09 g/mL. The secreted extracellular glycolipids have significantly lower processing costs because the costs of lysing of cells and separation of oil from cell debris can be eliminated or greatly reduced.

In varying embodiments, the methods further comprise the step of isolating and/or purifying the one or more glycolipids from the yeast culture. Because the glycolipids are extracellularly secreted from the yeast cells, and the yeast cell culture does not contain a hydrophobic carbon source, the one or more glycolipids can be isolated and/or purified from the yeast cell culture without cell lysis or extraction requiring an organic solvent. The secreted glycolipid compounds are denser than water and can be recovered inexpensively using separation methods based on density such as centrifugation, continuous decanting, or simply letting the material settle to the bottom of a container. Accordingly, in varying embodiments, the basidiomycetous yeast cells can be cultured under batch, fed-batch or continuous feed processing conditions. In varying embodiments, using batch, fed-batch or continuous feed cultivation conditions in which the culture is repeatedly or continuously fed allowing the cells to continue producing product, up to several hundred grams of substrate e.g., 100 g, 150 g, 200 g, 250 g, 300 g, 350 g, 400 g, 450 g or 500 g) per liter can be obtained.

Embodiments of the one or more glycolipids and glycolipid composition profiles produced according to the methods are as described below.

3. Glycolipids and Glycolipid Profiles Produced According to the Methods

Glycolipid biosurfactants include rhamnolipids, sophoroselipids, glucoselipids, cellobioselipids, trehaloselipids, and mannosylerythritol lipids. In varying embodiments, the one or more glycolipids in the yeast cultures, produced according to the methods, and/or in the glycolipid compositions isolated and/or purified from the yeast cultures comprise one or more rhamnolipids, sophoroselipids, glucoselipids, cellobioselipids, trehaloselipids, and/or mannosylerythritol lipids. In varying embodiments, the one or more glycolipids in the yeast cultures, produced according to the methods, and/or in the glycolipid compositions isolated and/or purified from the yeast cultures comprise one or more sophoroselipids or sophorolipids (SL). In varying embodiments, the one or more glycolipids are free of any hydrophobic carbon source, as discussed above.

Sophorolipids (SL) are non-petroleum based, biodegradable glycolipid biosurfactants on the market in household and industrial cleaners and in agricultural pest control products, with many more potential uses. Sophorolipids are composed of the disaccharide sophorose linked to a hydroxyl fatty acyl moiety by a glycosidic bond omega or omega-1 C of the fatty acid and the 1' —OH group of the sophorose sugar. The 6' or 6" OH group of either glucose may or may not be acetylated. When mono-acetylated or di-acetylated, the location of acetylation can be either or both the 6' or 6" OH group of either glucose. The fatty acid chain length varies from 16 to 20 carbon atoms, and may be saturated or unsaturated. The sugar can be attached to any carbon of the fatty acid. In some embodiments, the sugar can be attached only to the omega or omega-1 carbon (C) of the fatty acid (the acidic form), or also to the carboxylic acid group of the fatty acid (the lactone form). In varying embodiments, the one or more glycolipids produced are a mixture of similar compounds comprised of C16:1, C18:1, C20:1 and C22:1 fatty acids covalently attached or linked to the disaccharide of glucose comprising sophorose (2-O-beta-D-glucopyranosyl-alpha-D-glucose) (see FIG. 3). In varying embodiments, the one or more glycolipids comprise lactonized forms of SL. In varying embodiments, the one or more glycolipids comprise acid forms of SL. In varying embodiments, the fatty acid is attached to the 1' carbon of the first glucose unit and the carboxyl group is linked to the 4" OH group of the second unit forming a lactone.

In varying embodiments, the one or more glycolipids in the yeast cultures, produced according to the methods, and/or in the glycolipid compositions isolated and/or purified from the yeast cultures comprise one or more glycolipids listed in Table 2, below. In varying embodiments, the glycolipid sugar moiety or glycan comprises a disaccharide of glucose. In varying embodiments, the disaccharide of glucose comprises sophorose or cellobiose. In varying embodiments, the one or more glycolipids comprise a fatty acid comprising from 14 to 24 carbon atoms in length. In some embodiments, the glycolipid sugar moiety or glycan is attached or bound to the omega or omega-1 carbon of the fatty acid. In some embodiments, the glycolipid sugar moiety or glycan is attached or bound to a central carbon of the fatty acid. In varying embodiments, the glycolipid sugar moiety or glycan is attached or bound to carbon that is not the alpha carbon (carboxyl carbon, C1) of the fatty acid. In varying embodiments, the glycolipid sugar moiety or glycan can be non-acetylated, monoacetylated or diacetylated. In varying embodiments, the monoacetylated glycolipids comprise an acyl group on the 6' carbon or the 6" carbon of the disaccharide of glucose.

In varying embodiments, the one or more glycolipids in the yeast cultures, produced according to the methods, and/or in the glycolipid compositions isolated and/or purified from the yeast cultures comprise a glycolipid profile comprising:

i) at least about 20%, e.g., at least about 20%, 25%, 30%, 35%, 40%, up to about 45%, of a lactonic glycolipid with C18:2 fatty acid methylester or odd/branched chain length (Molecular Formula: C31H52O12);

ii) at least about 5%, e.g., at least about 10%, 15%, 20%, up to about 25%, of a lactonic glycolipid with C20:0 fatty acid methylester or odd/branched chain length (Molecular Formula: C33H56O12); and/or iii) at least about 5%, e.g., at least about 10%, 15%, up to about 20%, of a monoacetylated lactonic glycolipid with C20:1 fatty acid (Molecular Formula: C34H58O13).

In varying embodiments, the one or more glycolipids in the yeast cultures, produced according to the methods, and/or in the glycolipid compositions isolated and/or purified from the yeast cultures comprise a glycolipid profile comprising a glycolipid profile comprising at least about 25% of a lactonic glycolipid with C18:2 FA methylester or odd/branched chain length (Molecular Formula: C31H52O12).

In varying embodiments, the one or more glycolipids in the yeast cultures, produced according to the methods, and/or in the glycolipid compositions isolated and/or purified from the yeast cultures comprise a glycolipid profile comprising:

i) at least about 5%, e.g., at least about 6%, 7%, 8%, 9%, 10%, up to about 12%, of a lactonic glycolipid with C20:1 Fatty acid (Molecular Formula: C32H56O12);

ii) at least about 7%, e.g., at least about 8%, 9%, 10%, 11%, 12%, 13%, 14%, 15%, 16%, up to about 20%, of a monoacetylated lactonic glycolipid with C18:1 Fatty acid (Molecular Formula: C32H54O13);

iii) at least about 10%, e.g., at least about 11%, 12%, 13%, 14%, 15%, 16%, 17%, 18%, 19%, 20%, up to about 25%, of a monoacetylated lactonic glycolipid with C20:1 Fatty acid (Molecular Formula: C34H58O13);

iv) at least about 15%, e.g., at least about 20%, 25%, 30%, 35%, 40%, 45%, up to 50%, of a lactonic glycolipid with C18:2 Fatty acid methylester (Molecular Formula: C31H52O12); and/or v) at least about 10%, e.g., at least about 15%, 20%, 25%, 30%, up to 35%, of a lactonic glycolipid with C20:0 Fatty acid methylester (Molecular Formula: C33H56O12). In some embodiments, the yeast culture further comprises:

vi) at least about 2%, e.g., at least about 3%, 4%, 5%, 6%, 7%, 8%, 9%, 10%, up to about 12%, of a diacetylated lactonic glycolipid with C18:1 Fatty acid (Molecular Formula: C34H56O14); and/or vii) at least about 1%, e.g., at least about 2%, 3%, 4%, 5%, 6%, 7%, 8%, 9%, 10%, up to about 12%, of a diacetylated lactonic glycolipid with C20:1 Fatty acid (Molecular Formula: C36H60O14).

In varying embodiments, the one or more glycolipids in the yeast cultures, produced according to the methods, and/or in the glycolipid compositions isolated and/or purified from the yeast cultures comprise a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid with C20:1 Fatty acid (Molecular Formula: C34H58O13);

ii) at least about 15%, e.g., at least about 20%, 25%, 30%, 35%, 40%, up to about 45%, of a diacetylated lactonic glycolipid with C18:1 Fatty acid (Molecular Formula: C34H56O14);

iii) at least about 10%, e.g., at least about 11%, 12%, 13%, 14%, 15%, 16%, 17%, 18%, 19%, 20%, up to about 25%, of a diacetylated lactonic glycolipid with C20:1 Fatty acid (Molecular Formula: C36H60O14);

iv) at least about 15%, e.g., at least about 20%, 25%, 30%, 35%, 40%, up to about 45%, of a lactonic glycolipid with C18:2 Fatty acid methylester (Molecular Formula: C31H52O12); and/or v) at least about 15%, e.g., at least about 20%, 25%, 30%, 35%, 40%, up to about 45%, of a lactonic glycolipid with C20:0 Fatty acid methylester (Molecular Formula: C33H56O12).

In varying embodiments, the one or more glycolipids in the yeast cultures, produced according to the methods, and/or in the glycolipid compositions isolated and/or purified from the yeast cultures comprise a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid with C20:1 Fatty acid (Molecular Formula: C34H58O13);

ii) at least about 25%, e.g., at least about 30%, 35%, 40%, 45%, up to 50%, of a diacetylated lactonic glycolipid with C18:1 Fatty acid (Molecular Formula: C34H56O14);

iii) at least about 15%, e.g., at least about 20%, 25%, 30%, 35%, 40%, 45%, up to 50%, of a diacetylated lactonic glycolipid with C20:1 Fatty acid (Molecular Formula: C36H60O14);

iv) at least about 5%, e.g., at least about 6%, 7%, 8%, 9%, 10%, up to about 12%, of a lactonic glycolipid with C18:2 Fatty acid methylester (Molecular Formula: C31H52O12); and/or v) at least about 15%, e.g., at least about 20%, 25%, 30%, 35%, 40%, up to about 45%, of a lactonic glycolipid with C20:0 Fatty acid methylester (Molecular Formula: C33H56O12).

In varying embodiments, the one or more glycolipids in the yeast cultures, produced according to the methods, and/or in the glycolipid compositions isolated and/or purified from the yeast cultures comprise a glycolipid profile comprising:

i) at least about 5%, e.g., at least about 6%, 7%, 8%, 9%, 10%, up to about 12%, of a monoacetylated lactonic glycolipid with C20:1 Fatty acid (Molecular Formula: C34H58O13);

ii) at least about 10%, e.g., at least about 11%, 12%, 13%, 14%, 15%, 16%, 17%, 18%, 19%, 20%, up to about 25%, of a diacetylated lactonic glycolipid with C18:1 Fatty acid (Molecular Formula: C34H56O14);

iii) at least about 5%, e.g., at least about 6%, 7%, 8%, 9%, 10%, up to about 12%, of a diacetylated lactonic glycolipid with C20:1 Fatty acid (Molecular Formula: C36H60O14);

iv) at least about 15%, e.g., at least about 20%, 25%, 30%, 35%, 40%, up to about 45%, of a lactonic glycolipid with C18:2 Fatty acid methylester (Molecular Formula: C31H52O12); and/or v) at least about 40%, e.g., up to about 50%, of a lactonic glycolipid with C20:0 Fatty acid methylester (Molecular Formula: C33H56O12).

In varying embodiments, the one or more glycolipids in the yeast cultures, produced according to the methods, and/or in the glycolipid compositions isolated and/or purified from the yeast cultures comprise a glycolipid profile comprising:

i) at least about 10%, e.g., at least about 11%, 12%, 13%, 14%, 15%, 16%, 17%, 18%, 19%, 20%, up to about 25%, of a monoacetylated lactonic glycolipid with C18:1 Fatty acid (Molecular Formula: C32H54O13);

ii) at least about 45% of a lactonic glycolipid with C18:2 Fatty acid methylester (Molecular Formula: C31H52O12); and/or iii) at least about 5%, e.g., at least about 6%, 7%, 8%, 9%, 10%, up to about 12%, of a lactonic glycolipid with C20:0 Fatty acid methylester (Molecular Formula: C33H56O12).

In varying embodiments, the one or more glycolipids are selected from those listed in Table 2. In varying embodiments, the population of yeast cells in the yeast cell culture produces one or more glycolipids having a glycolipid profile according to the glycolipid profiles provided in Tables 3a-d.

TABLE 2

| GL_# | Chemical Formula | Molecular Weight (g/mol) | RT (min) | Description | Systematic Name |
|---|---|---|---|---|---|
| 1 | C28H48O12 | 576.69 | 1.72 | Lactonic glycolipid with C16:1 Fatty acid | 9-Hexadecenoic acid, 15-[(2-O-β-D-glucopyranosyl-β-D-glucopyranosyl)oxy]-, intramol. 1,4″-ester |
| 2 | C30H52O12 | 604.75 | 2.48 | Lactonic glycolipid with C18:1 Fatty acid | 9-Octadecenoic acid, 17-[(2-O-β-D-glucopyranosyl-β-D-glucopyranosyl)oxy]-, intramol. 1,4″-ester |
| 3 | C32H56O12 | 632.80 | 3.12 | Lactonic glycolipid with C20:1 Fatty acid | 11-Eicosanoic acid, 19-[(2-O-β-D-glucopyranosyl-β-D-glucopyranosyl)oxy]-, intramol. 1,4″-ester |
| 4 | C34H60O12 | 660.86 | 3.52 | Lactonic glycolipid with C22:1 Fatty acid | 13-Docosenoic acid, 21-[(2-O-β-D-glucopyranosyl-β-D-glucopyranosyl)oxy]-, intramol. 1,4″-ester |
| 5 | C30H50O13 | 618.73 | 2.10 | Monoacetylated Lactonic glycolipid with C16:1 Fatty acid | 9-Hexadecenoic acid, 15-[(6-O-acetyl-2-O-β-D-glucopyranosyl-β-D-glucopyranosyl)oxy]-, intramol. 1,4″-ester or 9-Hexadecenoic acid, 15-[[2-O-(6-O-acetyl-β-D-glucopyranosyl)-β-D-glucopyranosyl]oxy]-, intramol. 1,4″-ester |
| 6 | C32H54O13 | 646.79 | 2.87 | Monoacetylated Lactonic glycolipid with C18:1 Fatty acid | 9-Octadecenoic acid, 17-[(6-O-acetyl-2-O-β-D-glucopyranosyl-β-D-glucopyranosyl)oxy]-, intramol. 1,4″-ester or 9-Octadecenoic acid, 17-[[2-O-(6-O-acetyl-β-D-glucopyranosyl)-β-D-glucopyranosyl]oxy]-, intramol. 1,4″-ester |
| 7 | C34H58O13 | 674.84 | 3.29 | Monoacetylated Lactonic glycolipid with C20:1 Fatty acid | 11-Eicosanoic acid, 19-[(6-O-acetyl-2-O-β-D-glucopyranosyl-β-D-glucopyranosyl)oxy]-, intramol. 1,4″-ester or 11-Eicosanoic acid, 19-[[2-O-(6-O-acetyl-β-D-glucopyranosyl)-β-D-glucopyranosyl]oxy]-, intramol. 1,4″-ester |
| 8 | C36H62O13 | 702.89 | 3.69 | Monoacetylated Lactonic glycolipid with C22:1 Fatty acid | 13-Docosenoic acid, 21-[(6-O-acetyl-2-O-β-D-glucopyranosyl-β-D-glucopyranosyl)oxy]-, intramol. 1,4″-ester or 13-Docosenoic acid, 21-[[2-O-(6-O-acetyl-β-D-glucopyranosyl)-β-D-glucopyranosyl]oxy]-, intramol. 1,4″-ester |
| 9 | C30H48O14 | 632.71 | 1.79 | Diacetylated Lactonic glycolipid with C14:1 Fatty acid | 9-Tetradecenoic acid, 13-[[6-O-acetyl-2-O-(6-O-acetyl-β-D-glucopyranosyl)-β-D-glucopyranosyl]oxy]-, intramol. 1,4″-ester |
| 10 | C32H52O14 | 660.77 | 2.52 | Diacetylated Lactonic glycolipid with C16:1 Fatty acid | 9-Hexadecenoic acid, 15-[[6-O-acetyl-2-O-(6-O-acetyl-β-D-glucopyranosyl)-β-D-glucopyranosyl]oxy]-, intramol. 1,4″-ester |
| 11 | C34H56O14 | 688.82 | 3.10 | Diacetylated Lactonic glycolipid with C18:1 Fatty acid | 9-Octadecenoic acid, 17-[[6-O-acetyl-2-O-(6-O-acetyl-β-D-glucopyranosyl)-β-D-glucopyranosyl]oxy]-, intramol. 1,4″-ester |
| 12 | C36H60O14 | 716.88 | 3.47 | Diacetylated Lactonic glycolipid with C20:1 Fatty acid | 11-Eicosanoic acid, 19-[[6-O-acetyl-2-O-(6-O-acetyl-β-D-glucopyranosyl)-β-D-glucopyranosyl]oxy]-, intramol. 1,4″-ester |
| 13 | C31H52O12 | 616.76 | 3.07 | Lactonic glycolipid with C18:2 Fatty acid methylester | Methyl 9,12-octadecadienoate 17-[(2-O-β-D-glucopyranosyl-β-D-glucopyranosyl)oxy]-, intramol. 1,4″-ester |
| 14 | C33H56O12 | 644.81 | 3.45 | Lactonic glycolipid with C20:0 Fatty acid methylester | Methyl eicosanoate 19-[(2-O-β-D-glucopyranosyl-β-D-glucopyranosyl)oxy]-, intramol. 1,4″-ester |
| 15 | C32H54O13 | 646.79 | 1.08 | Acidic glycolipid with C20:3 Fatty acid | Eicosatrienoic acid, 19-[(2-O-β-D-glucopyranosyl-β-D-glucopyranosyl)oxy]-, |
| 16 | C32H54O14 | 662.78 | 1.31 | Monoacetylated acidic glycolipid with C18:2 Fatty acid | 9,12-Octadecadienoic acid, 17-[(6-O-acetyl-2-O-β-D-glucopyranosyl-β-D-glucopyranosyl)oxy]-, or 9,12-Octadecadienoic acid, 17-[[2-O-(6-O-acetyl-β-D-glucopyranosyl)-β-D-glucopyranosyl]oxy]-, |

TABLE 2-continued

| GL_# | Chemical Formula | Molecular Weight (g/mol) | RT (min) | Description | Systematic Name |
|---|---|---|---|---|---|
| 17 | C34H58O14 | 690.84 | 1.87 | Monoacetylated acidic glycolipid with C20:2 Fatty acid | 11,14-Eicosadienoic acid, 19-[(6-O-acetyl-2-O-β-D-glucopyranosyl-β-D-glucopyranosyl)oxy]-, or 11,14-Eicosadienoic acid, 19-[[2-O-(6-O-acetyl-β-D-glucopyranosyl)-β-D-glucopyranosyl]oxy]-, |
| 18 | C34H56O14 | 688.82 | 1.08 | Monoacetylated acidic glycolipid with C20:3 Fatty acid | Eicosatrienoic acid, 19-[(6-O-acetyl-2-O-β-D-glucopyranosyl-β-D-glucopyranosyl)oxy]-, or Eicosatrienoic acid, 19-[[2-O-(6-O-acetyl-β-D-glucopyranosyl)-β-D-glucopyranosyl]oxy]-, |
| 19 | C36H66O14 | 722.93 | 1.44 | Monoacetylated acidic glycolipid with C22:0 Fatty acid (isomer A) | Docosanoic acid, 21-[(6-O-acetyl-2-O-β-D-glucopyranosyl-β-D-glucopyranosyl)oxy]-, or Docosanoic acid, 21-[(6-O-acetyl-2-O-β-D-glucopyranosyl-β-D-glucopyranosyl)oxy]-, |
| 20 | C36H66O14 | 722.93 | 1.59 | Monoacetylated acidic glycolipid with C22:0 Fatty acid (isomer B) | Docosanoic acid, 21-[(6-O-acetyl-2-O-β-D-glucopyranosyl-β-D-glucopyranosyl)oxy]-, or Docosanoic acid, 21-[(6-O-acetyl-2-O-β-D-glucopyranosyl-β-D-glucopyranosyl)oxy]-, |
| 21 | C32H54O15 | 678.78 | 0.55 | Diacetylated acidic glycolipid with C16:1 Fatty acid | 9-Hexadecenoic acid, 15-[[6-O-acetyl-2-O-(6-O-acetyl-β-D-glucopyranosyl)-β-D-glucopyranosyl]oxy]-, |
| 22 | C34H58O15 | 706.84 | 0.80 | Diacetylated acidic glycolipid with C18:1 Fatty acid | 9-Octadecenoic acid, 17-[[6-O-acetyl-2-O-(6-O-acetyl-β-D-glucopyranosyl)-β-D-glucopyranosyl]oxy]-, |
| 23 | C38H68O15 | 764.96 | 1.88 | Diacetylated acidic glycolipid with C22:0 Fatty acid | Docosanoic acid, 21-[[6-O-acetyl-2-O-(6-O-acetyl-β-D-glucopyranosyl)-β-D-glucopyranosyl]oxy]-, |
| 24 | C40H72O15 | 793.02 | 2.57 | Diacetylated acidic glycolipid with C24:0 Fatty acid | Tetracosanoic acid, 23-[[6-O-acetyl-2-O-(6-O-acetyl-β-D-glucopyranosyl)-β-D-glucopyranosyl]oxy]-, |
| 25 | C39H70O15 | 778.99 | 2.23 | Diacetylated acidic SL with C22:0 Fatty acid methylester | Methyl docosanoate, 21-[[6-O-acetyl-2-O-(6-O-acetyl-β-D-glucopyranosyl)-β-D-glucopyranosyl]oxy]-, |
| 26 | C29H50O11 | 574.720 | | | Unknown (C29H50O11) |
| 27 | C31H54O11 | 602.775 | | | Unknown (C31H54O11) |
| 28 | C30H54O11 | 590.764 | | | Unknown (C30H54O11) |

Tables 3A-D

Profiles of Glycolipid Species Produced by Basidiomycetous Yeast Species in the Phaff Yeast Culture Collection.

TABLE 3A

| Yeast Strain | NRRL strain ID | UCDFST strain ID | GL_01 | GL_02 | GL_03 | GL_04 | GL_05 | GL_06 | GL_07 |
|---|---|---|---|---|---|---|---|---|---|
| Rhodotorula aff. paludigena (syn. Rhodosporidium aff. paludigenum) | Y-67009 | 81-84 | 0.0097 | 0.1035 | 0.0489 | 0.0029 | 0.0102 | 0.06 | 0.026 |
| Rhodotorula babjevae (syn. Rhodosporidium babjevae) | Y-67018 | 04-877 | 0.0422 | 3.5806 | 5.8705 | 0.0233 | 0.1078 | 8.9467 | 11.1175 |
| Rhodotorula babjevae (syn. Rhodosporidium babjevae) | Y-67017 | 05-775 | 0.0824 | 4.323 | 6.0044 | 0.0249 | 0.1645 | 13.4006 | 15.3295 |
| Rhodosporidiobolus aff. colostri (syn. Rhodotorula aff. colostri) | Y-67014 | 06-583 | 0.0445 | 2.5715 | 5.5554 | 0.4142 | 0.2669 | 8.4284 | 11.9318 |
| Rhodotorula sphaerocarpa (syn. Rhodosporidium sphaerocarpum) | Y-67010 | 68-43 | 0.625 | 2.7409 | 5.1914 | 1.1312 | 0.0237 | 8.8468 | 12.3729 |
| Rhodotorula kratochvilovae (syn. Rhodosporidium kratochvilovae) | Y-67016 | 05-632 | 0.0001 | 0.0203 | 0.3509 | 0.0364 | 0.0084 | 0.4387 | 11.1815 |
| Rhodosporidiobolus aff. nylandii (syn. Sporobolomyces aff. nylandii) | Y-67013 | 09-1303 | 0.1988 | 3.6513 | 5.6073 | 0.8772 | 0.5624 | 8.1274 | 12.3984 |
| Rhodotorula paludigena (syn. Rhodosporidium paludigenum) | Y-67012 | 09-163 | 0.161 | 2.7162 | 2.3632 | 0.0137 | 0.3586 | 16.7612 | 7.0736 |
| Rhodosporidiobolus ruineniae (syn. Sporidiobolus ruineniae) | Y-17302 | 67-67 | 0.1096 | 1.3283 | 5.5552 | 0.0278 | 0.1222 | 3.3346 | 5.8014 |
| Pseudohyphozyma bogoriensis, (syn. Rhodotorula bogoriensis) | Y-12675 | 67-20 | 0.0023 | 0.0546 | 0.0997 | 0.0151 | 0.0081 | 0.1774 | 0.2414 |

TABLE 3A-continued

| Yeast Strain | NRRL strain ID | UCDFST strain ID | GL_01 | GL_02 | GL_03 | GL_04 | GL_05 | GL_06 | GL_07 |
|---|---|---|---|---|---|---|---|---|---|
| *Rhodotorula diobovata* (syn. *Rhodosporidioum diobovatum*) | Y-67015 | 08-225 | 0.0033 | 0.1039 | 1.0969 | 0.0237 | 0.0068 | 0.8164 | 16.9191 |
| *Starmerella bombicola* | Y-17069 | 10-162 | 0.0074 | 0.0608 | 0.1502 | 0.006 | 0.01 | 0.2298 | 0.3757 |
| *Rhodotorula dairenensis* | Y-67011 | 68-257 | 0.0028 | 0.0549 | 0.3584 | 0.0161 | 0.0001 | 2.8791 | 6.0896 |

GL_01, GL_02, etc: glycolipid species listed in Table 2. nd: not detected. Each value is the percent of total glycolipids for that strain. "aff." (affinis) means a new species most closely related to the named species. Yeasts were deposited in the USDA-ARS patent repository in Peoria, Ill., USDA, except strains NRRL Y-12675 and Y-17069 which were already present in the NRRL main collection. NRRL strain ID numbers are listed.

TABLE 3B

| Yeast Strain | NRRL strain ID | UCDFST strain ID | GL_08 | GL_09 | GL_10 | GL_11 | GL_12 | GL_13 | GL_14 |
|---|---|---|---|---|---|---|---|---|---|
| *Rhodotorula* aff. *paludigena* (syn. *Rhodosporidium* aff. *paludigenum*) | Y-67009 | 81-84 | 0.003 | 0.001 | 0.0026 | 0.0118 | 0.0052 | 27.7663 | 3.4103 |
| *Rhodotorula babjevae* (syn. *Rhodosporidium babjevae*) | Y-67018 | 04-877 | 0.0344 | 0.0147 | 0.1147 | 3.4372 | 1.5044 | 29.921 | 22.037 |
| *Rhodotorula babjevae* (syn. *Rhodosporidium babjevae*) | Y-67017 | 05-775 | 0.0411 | 0.0105 | 0.0874 | 2.3449 | 0.9736 | 25.4548 | 14.5552 |
| *Rhodosporidiobolus* aff. *colostri* (syn. *Rhodotorula* aff. *colostri*) | Y-67014 | 06-583 | 0.4693 | 0.0057 | 0.3564 | 3.5429 | 1.8015 | 29.8501 | 13.7706 |
| *Rhodotorula sphaerocarpa* (syn. *Rhodosporidium sphaerocarpum*) | Y-67010 | 68-43 | 1.5099 | 0.4612 | 0.0237 | 2.9266 | 2.2824 | 21.1511 | 11.3258 |
| *Rhodotorula kratochvilovae* (syn. *Rhodosporidium kratochvilovae*) | Y-67016 | 05-632 | 0.0588 | 0.0012 | 0.4687 | 19.1007 | 13.2349 | 25.3099 | 22.1654 |
| *Rhodosporidiobolus* aff. *nylandii* (syn. *Sporobolomyces* aff. *nylandii*) | Y-67013 | 09-1303 | 2.3467 | 0.0312 | 0.0312 | 3.9761 | 2.3535 | 22.1001 | 8.4611 |
| *Rhodotorula paludigena* (syn. *Rhodosporidium paludigenum*) | Y-67012 | 09-163 | 0.0169 | 0.0093 | 0.1075 | 1.5562 | 0.2294 | 48.725 | 7.5512 |
| *Rhodosporidiobolus ruineniae* (syn. *Sporidiobolus ruineniae*) | Y-17302 | 67-67 | 0.1573 | 0.1024 | 0.1966 | 4.4139 | 1.9813 | 30.1747 | 21.6825 |
| *Pseudohyphozyma bogoriensis* (syn. *Rhodotorula bogoriensis*) | Y-12675 | 67-20 | 0.0211 | 0.013 | 0.0003 | 0.0628 | 0.0441 | 0.3079 | 0.1594 |
| *Rhodotorula diobovata* (syn. *Rhodosporidium diobovatum*) | Y-67015 | 08-225 | 0.112 | 0.0022 | 0.1926 | 30.7457 | 22.3245 | 7.7966 | 18.4463 |
| *Starmerella bombicola* | Y-17069 | 10-162 | 0.0127 | 0.0069 | 0.0003 | 0.1976 | 0.0803 | 0.8978 | 0.4493 |
| *Rhodotorula dairenensis* | Y-67011 | 68-257 | 0.0076 | 0.0022 | 0.0095 | 12.406 | 9.0879 | 23.1439 | 43.9026 |

TABLE 3C

| Yeast Strain | NRRL strain ID | UCDFST Strain ID | GL_15 | GL_16 | GL_17 | GL_18 | GL_19 | GL_20 | GL_21 |
|---|---|---|---|---|---|---|---|---|---|
| *Rhodotorula* aff. *paludigena* (syn. *Rhodosporidium* aff. *paludigenum*) | Y-67009 | 81-84 | 0.0014 | 0.0001 | 0.0001 | 0.001 | 0.0001 | 0.0017 | 0.0001 |
| *Rhodotorula babjevae* (syn. *Rhodosporidium babjevae*) | Y-67018 | 04-877 | 0.0008 | 0.0022 | nd | 0.0013 | 0.003 | 0.0032 | 0.0025 |
| *Rhodotorula babjevae* (syn. *Rhodosporidium babjevae*) | Y-67017 | 05-775 | nd | 0.002 | 0.0008 | 0.0008 | 0.0016 | 0.0017 | nd |
| *Rhodosporidiobolus* aff. *colostri* (syn. *Rhodotorula* aff. *colostri*) | Y-67014 | 06-583 | 0.264 | 0.151 | 0.0057 | 0.1183 | 0.0057 | 0.0057 | 0.3572 |
| *Rhodotorula sphaerocarpa* (syn. *Rhodosporidium sphaerocarpum*) | Y-67010 | 68-43 | 1.3381 | 0.7028 | 0.4627 | 0.555 | 1.902 | 1.902 | 0.0237 |
| *Rhodotorula kratochvilovae* (syn. *Rhodosporidium kratochvilovae*) | Y-67016 | 05-632 | nd | nd | 0.0004 | nd | nd | nd | 0.0003 |
| *Rhodosporidiobolus* aff. *nylandii* (syn. *Sporobolomyces* aff. *nylandii*) | Y-67013 | 09-1303 | 0.7036 | 0.6757 | 0.0312 | 0.0312 | 1.525 | 1.5496 | 0.5659 |

TABLE 3C-continued

| Yeast Strain | NRRL strain ID | UCDFST Strain ID | GL_15 | GL_16 | GL_17 | GL_18 | GL_19 | GL_20 | GL_21 |
|---|---|---|---|---|---|---|---|---|---|
| Rhodotorula paludigena (syn. Rhodosporidium paludigenum) | Y-67012 | 09-163 | 0.0037 | 0.0041 | 0.0001 | 0.0001 | 0.0001 | 0.0027 | 0.0039 |
| Rhodosporidiobolus ruineniae (syn. Sporidiobolus ruineniae) | Y-17302 | 67-67 | 0.1228 | 0.0478 | 0.0026 | 0.0588 | 0.1016 | 0.106 | 0.2539 |
| Pseudohyphozyma bogoriensis, (syn. Rhodotorula bogoriensis) | Y-12675 | 67-20 | 0.0049 | 0.0183 | 0.007 | 0.0003 | 0.8678 | 0.8046 | 0.0003 |
| Rhodotorula diobovata (syn. Rhodosporidium diobovatum) | Y-67015 | 08-225 | nd | 0.0007 | nd | 0.0007 | 0.0028 | 0.0036 | 0.0023 |
| Starmerella bombicola | Y-17069 | 10-162 | 52.3762 | 9.4158 | 17.0036 | 1.4493 | 0.0118 | 0.0118 | 3.5172 |
| Rhodotorula dairenensis | Y-67011 | 68-257 | 0.0039 | 0.0056 | 0.0017 | 0.0001 | 0.0043 | 0.0048 | 0.0047 |

TABLE 3D

| Yeast Strain | NRRL strain ID | UCDFST Strain ID | GL_22 | GL_23 | GL_24 | GL_25 | GL_26 | GL_27 | GL_28 |
|---|---|---|---|---|---|---|---|---|---|
| Rhodotorula aff. paludigena (syn. Rhodosporidium aff. paludigenum) | Y-67009 | 81-84 | 0.0011 | 0.001 | 0.001 | 0.0001 | 49.697 | 18.7635 | 0.0705 |
| Rhodotorula babjevae (syn. Rhodosporidium babjevae) | Y-67018 | 04-877 | nd | 0.0008 | 0.0016 | nd | 5.5728 | 7.5214 | 0.1382 |
| Rhodotorula babjevae (syn. Rhodosporidium babjevae) | Y-67017 | 05-775 | 0.0007 | 0.0011 | 0.0011 | 0.0011 | 7.958 | 8.9784 | 0.256 |
| Rhodosporidiobolus aff. colostri (syn. Rhodotorula aff. colostri) | Y-67014 | 06-583 | 0.2901 | 0.1342 | 0.0057 | 0.1349 | 9.8843 | 8.7178 | 0.9162 |
| Rhodotorula sphaerocarpa (syn. Rhodosporidium sphaerocarpum) | Y-67010 | 68-43 | 1.0222 | 0.487 | 0.487 | 0.6111 | 8.973 | 7.167 | 3.7537 |
| Rhodotorula kratochvilovae (syn. Rhodosporidium kratochvilovae) | Y-67016 | 05-632 | nd | 0.0008 | 0.0005 | 0.0004 | 2.8344 | 4.7757 | 0.0117 |
| Rhodosporidiobolus aff. nylandii (syn. Sporobolomyces aff. nylandii) | Y-67013 | 09-1303 | 0.0312 | 1.218 | 1.218 | 1.0796 | 8.8722 | 7.9423 | 3.8335 |
| Rhodotorula paludigena (syn. Rhodosporidium paludigenum) | Y-67012 | 09-163 | 0.003 | 0.0041 | 0.0025 | 0.0001 | 6.2906 | 5.828 | 0.214 |
| Rhodosporidiobolus ruineniae (syn. Sporidiobolus ruineniae) | Y-17302 | 67-67 | 0.0561 | 0.1194 | 0.1194 | 0.0026 | 7.7543 | 15.4439 | 0.8231 |
| Pseudohyphozyma bogoriensis, (syn. Rhodotorula bogoriensis) | Y-12675 | 67-20 | 0.0003 | 64.4957 | 31.7499 | 0.5594 | 0.1322 | 0.1121 | 0.0399 |
| Rhodotorula diobovata (syn. Rhodosporidium diobovatum) | Y-67015 | 08-225 | 0.0009 | nd | nd | 0.002 | 0.4403 | 0.9054 | 0.0513 |
| Starmerella bombicola | Y-17069 | 10-162 | 13.2706 | 0.0179 | 0.0119 | 0.0003 | 0.1787 | 0.2058 | 0.0444 |
| Rhodotorula dairenensis | Y-67011 | 68-257 | 0.0036 | 0.0029 | 0.0029 | 0.0015 | 0.225 | 1.7106 | 0.0678 |

4. Compositions Comprising Glycolipids

Further provided are compositions comprising the one or more glycolipids and/or having a glycolipid profile as described above and herein. Surfactants (both petroleum and bio-based) are used in a broad variety of agricultural, nutritional, cosmetic, veterinary, therapeutic, and industrial applications due to their many activities. Activities include cleansers, detergents, wetting agents, antifoam agents, emulsifiers, dispersants (e.g., for cleanup of oil including spilled petroleum), and humectants. They are used in household and industrial cleansers and detergents, textiles, agrochemicals, photo chemicals, petroleum extraction, construction materials, adhesives, lubricants, mining, and the pulp and paper industry. About half of surfactants are used in household and laundry detergents, and thus end up in the environment. The poor performance of petroleum-based surfactants with regard to sustainability, bio-accumulation, eco-toxicity and/or biodegradability is pushing development of bio-based replacements, or biosurfactants, which can be produced microbially from renewable feedstocks, have lower toxicity, and are biodegradable.

Major biosurfactants on the market include surfactin and emulsin, and a variety of glycolipids which are the major class of biosurfactants. Glycolipids including sophorolipids, rhamnolipids, trehalolipids, glucoselipids, cellobioselipids, and mannosylerythritol lipids have potential to be renewable, low-toxicity, biodegradable alternatives to petroleum-based surfactants. Rhamnolipids are produced by a pathogenic bacterium, Pseudomonas aeruginosa. Sophorolipids, produced by non-pathogenic yeasts, are currently on the market as detergents, emulsifiers, wetting agents, dispersants and other activities.

The acetylated lactone forms have been demonstrated to be effective additives in shampoos, body washes, detergents, and cosmetic products. There are conflicting reports of anti-bacterial activity. The acidic forms have been demonstrated to be effective ingredients in skin treatments and as moisturizing agents. Due to skin-friendly properties, both forms are also used in cosmetics and pharmaceuticals. Glycolipid esters have proven to be excellent moisturizers for cosmetic uses (See, e.g., U.S. Pat. No. 4,297,340).

Additional potential uses include spermicides and virucides (Shah, et al., *Antimicrob Agents Chemother.* (2005) 49(10): 4093-100), septic shock antagonists, anticancer agents and protein inducers/repressors in microbial systems (See, e.g., Intl. Publ. No. WO 2007/073371 A1). Derivatives and modified sophorolipids further have been shown to have antifungal activity (See, e.g., Intl. Publication No. WO2011/127101 and U.S. Patent Publication No. 2012/022241).

Accordingly, further provided are glycolipid compositions, e.g., comprising one or more of the glycolipids described above and herein, and produced by the methods described herein. Also contemplated are derivatives of the glycolipids described above and herein, and produced by the methods described herein, for example, derivatives of either the glycan or lipid moiety, including hydroxylated fatty acids, sophorose and derivatives, etc. In varying embodiments, the glycolipid composition is one or more of a cleanser, a detergent, a wetting agent, an antifoam agent, an emulsifier, a surfactant, an emollient, a dispersant, a humectant, an anti-bacterial agent, an anti-viral agent, an anti-fungal agent, a spermicide an insecticide, a lubricant, an adhesive, a crystal modifier, an instantizer, a viscosity modifier, a mixing/blending aid, and/or a release agent.

The glycolipid compositions find use in numerous applications, including without limitation, household and industrial cleansers and detergents, textiles, agrochemicals such as control of fungal and insect pests, food processing such as cleaning agents for fresh and frozen fruits, vegetables, meats and processed foods, food processing such as rheologic modifiers in food applications including doughs, pastas and emulsions such as mayonnaise, dressings, and syrups, food processing such as antiadherents, photo chemicals, petroleum extraction such as release agents for fracking, construction materials such as lubricants and demolding agents for brick, ceramic, cement and concrete, mining such as adjuvants in the coal industry, pulp and paper industry, cosmetics such as creams, foams, mousses, balms, ointments, personal care formulations such as shampoos, body washes, conditioners, soaps, creams, skin treatments, and moisturizing agents, therapeutics such as ointments and creams, spermicides, anti-viral and anti-cancer agents, leather auxiliary agents, fuel oil emulsification for improved atomization, yielding a more complete combustion, bioremediation of contaminated soils, groundwater and surface water, dust suppression in mines and quarries, release agents for asphalt truck beds, facilitates castable aqueous emulsions for the manufacture of explosives, ingredient in metal working fluids, and oleochemicals such as biodiesel, platform chemicals. Additional uses of the glycolipid compositions produced by the present methods are described, e.g., in U.S. Patent Publication Nos. 2012/0022241 and 2013/0072414, hereby incorporated herein by reference for all purposes.

EXAMPLES

The following examples are offered to illustrate, but not to limit the claimed invention.

Example 1

Pilot Study

Figure 2:
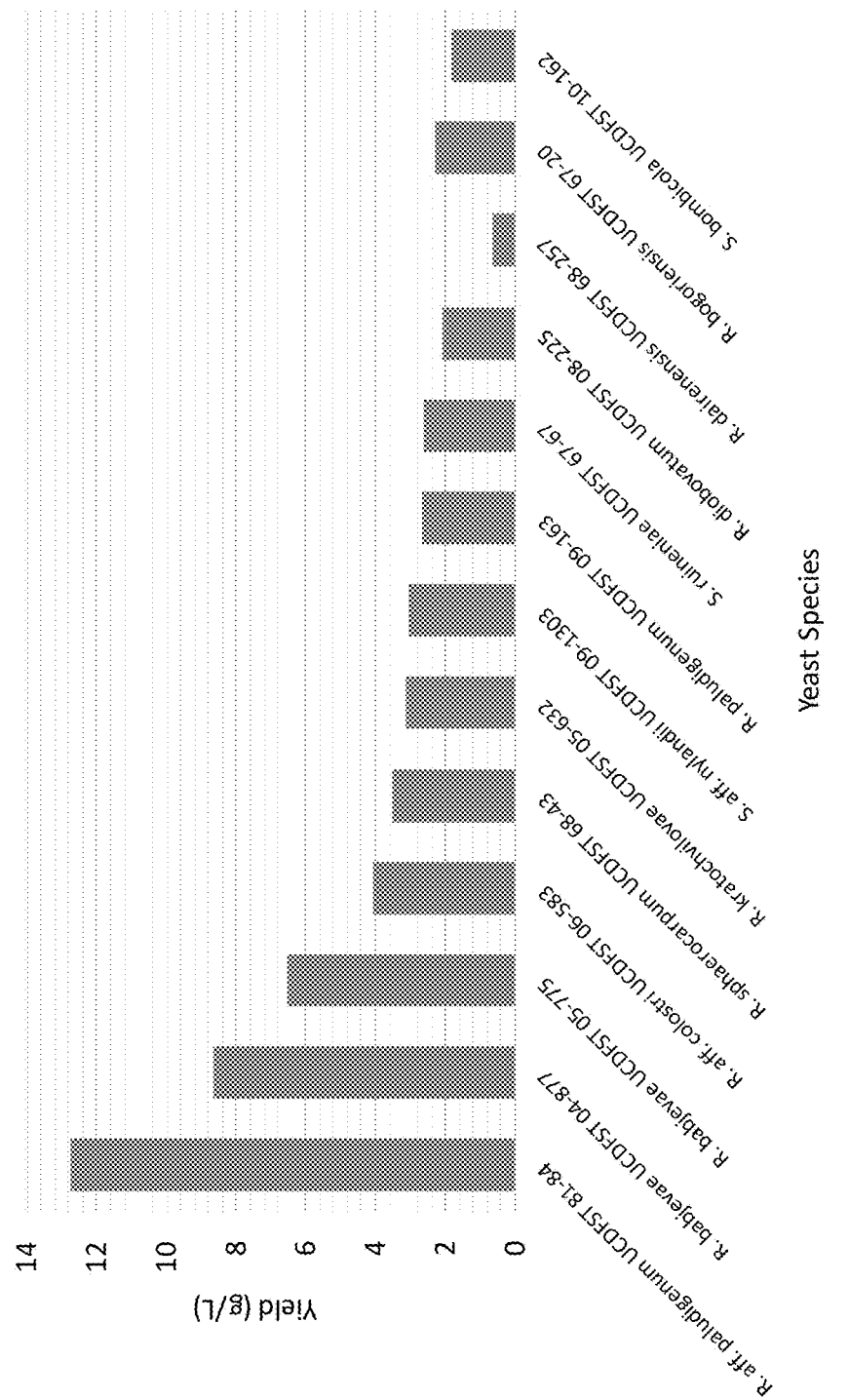
FIG. 2 illustrates the estimated extracellular lipid production (in units of g/L) by 12 yeast species, where the growth media contained 50 g/L glucose.

We performed a pilot study to determine whether additional related yeast species also secrete glycolipids. Sixteen of the 21 known species in the *Rhodotorula glutinis* clade, plus five novel species, were selected from the Phaff collection stocks and cultivated in Medium A [30], a glucose medium with high C/N ratio that induces lipid synthesis in these yeasts [31, 32]. Secreted glycolipid was quantified by decanting centrifuged cultures and/or by ethyl acetate extraction, followed by gravimetric analysis [12]. We identified 14 strains belonging to 12 species that secreted glycolipids, ranging from trace quantities up to an estimated 10-12 g/L crude product (FIG. 2 and Table 4).

TABLE 4

| Yeast Strain | NRRL strain ID | UCDFST Strain ID | Yields glycolipids (g/L culture) |
| --- | --- | --- | --- |
| *Rhodotorula* aff. *paludigena* (syn. *Rhodosporidium* aff. *paludigenum*) | Y-67009 | 81-84 | 12.74 |
| *Rhodotorula babjevae* (syn. *Rhodosporidium babjevae*) | Y-67018 | 04-877 | 8.67 |
| *Rhodotorula babjevae* (syn. *Rhodosporidium babjevae*) | Y-67017 | 05-775 | 6.53 |
| *Rhodosporidiobolus* aff. *colostri* (syn. *Rhodotorula* aff. *colostri*) | Y-67014 | 06-583 | 4.07 |
| *Rhodotorula sphaerocarpa* (syn. *Rhodosporidium sphaerocarpum*) | Y-67010 | 68-43M | 3.52 |
| *Rhodotorula kratochvilovae* (syn. *Rhodosporidium kratochvilovae*) | Y-67016 | 05-632 | 3.12 |
| *Rhodosporidiobolus* aff. *nylandii* (syn. *Sporobolomyces* aff. *nylandii*) | Y-67013 | 09-1303 | 3.04 |
| *Rhodotorula paludigena* (syn. *Rhodosporidium paludigenum*) | Y-67012 | 09-163 | 2.66 |
| *Rhodosporidiobolus ruineniae* (syn. *Sporidiobolus ruineniae*) | Y-17302 | 67-67 | 2.61 |
| *Pseudohyphozyma bogoriensis*, (syn. *Rhodotorula bogoriensis*) | Y-12675 | 67-20 | 2.29 |
| *Rhodotorula diobovata* (syn. *Rhodosporidium diobovatum*) | Y-67015 | 08-225 | 2.06 |
| *Starmerella bombicola* | Y-17069 | 10-162 | 1.84 |
| *Rhodotorula dairenensis* | Y-67011 | 68-257 | 0.62 |

Figure 3:
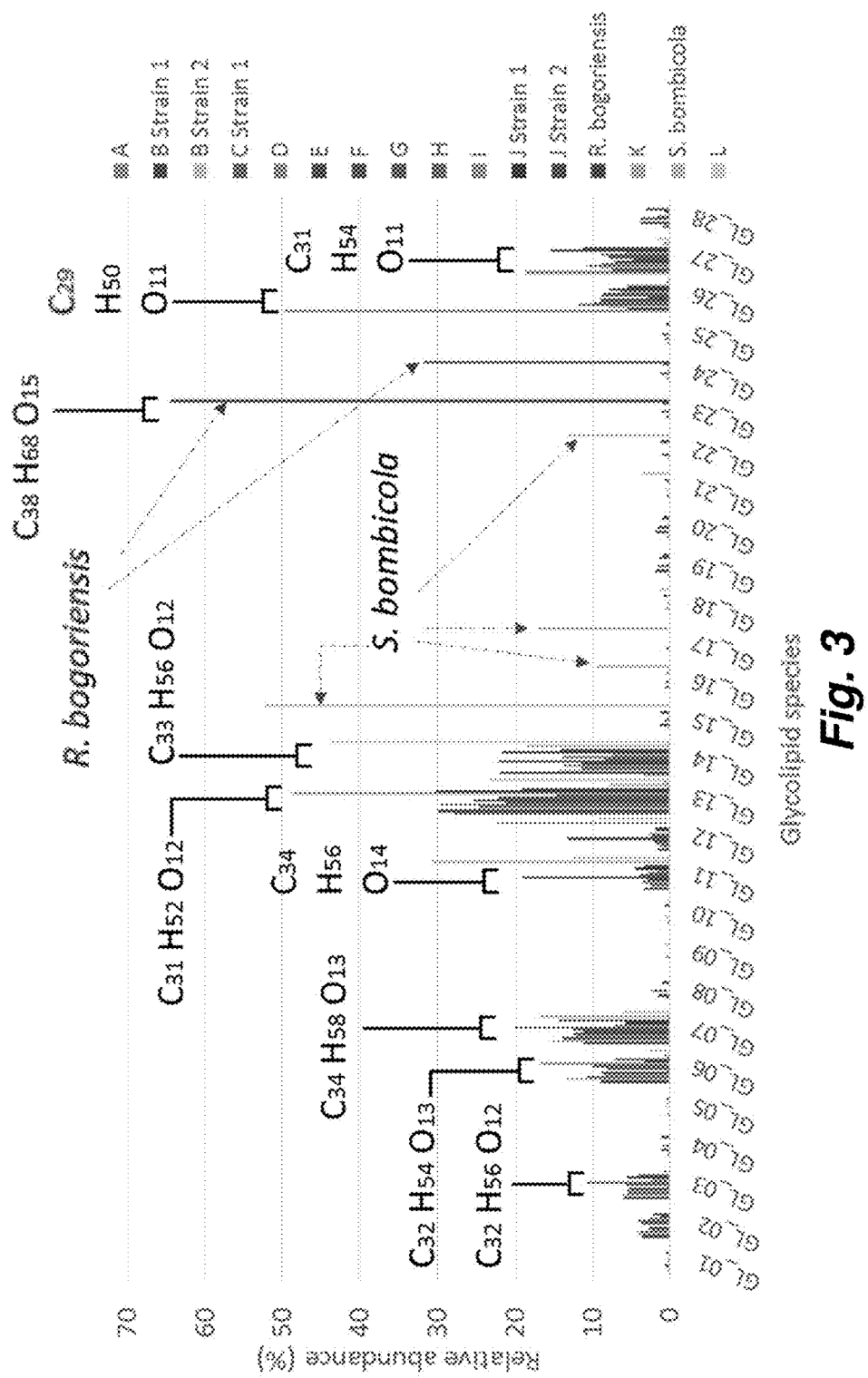
FIG. 3 illustrates the relative abundance of extracellular glycolipid species produced by our basidiomycetous yeasts, compared to those of *Starmerella bombicola* and *Pseudohyphozyma bogoriensis*, (syn. *Rhodotorula bogoriensis*). Glycolipid (GL)_01 through GL_28 are different glycolipid species, varying in fatty acid chain length, unsaturation, and acetylation of the carbohydrate. Molecular weights and formulas were determined. GL profiles of basidiomycetous yeasts in the taxonomic order Sporidiobolales are fairly similar to each other, but quite different from those of ascomycete *S. bombicola* or basidiomycete *Pseudohyphozyma bogoriensis*, (syn. *R. bogoriensis*).

We further identified the molecular weight and structural components of these glycolipids, shown in FIG. 3. The species codes are summarized in Table 5. The glycan is a disaccharide of glucose, e.g., a sophorose, as seen in glycolipids produced by other yeasts including *S. bombicola* and *Pseudohyphozyma bogoriensis*, (syn. *Rhodotorula bogoriensis*) [18, 33-36].

TABLE 5

| Species Code in FIGS. 1-3 | NRRL strain ID | UCDFST Strain ID | Species |
|---|---|---|---|
| A | Y-67009 | 81-84 | *Rhodotorula* aff. *paludigena* (syn. *Rhodosporidium* aff. *paludigenum*) |
| B Strain 1 | Y-67018 | 04-877 | *Rhodotorula babjevae* (syn. *Rhodosporidium babjevae*) |
| B Strain 2 | Y-67017 | 05-775 | *Rhodotorula babjevae* (syn. *Rhodosporidium babjevae*) |
| D | Y-67014 | 06-583 | *Rhodosporidiobolus* aff. *colostri* (syn. *Rhodotorula* aff. *colostri*) |
| E | Y-67010 | 68-43 | *Rhodotorula sphaerocarpa* (syn. *Rhodosporidium sphaerocarpum*) |
| F | Y-67016 | 05-632 | *Rhodotorula kratochvilovae* (syn. *Rhodosporidium kratochvilovae*) |
| G | Y-67013 | 09-1303 | *Rhodosporidiobolus* aff. *nylandii* (syn. *Sporobolomyces* aff. *nylandii*) |
| I | Y-67012 | 09-163 | *Rhodotorula paludigena* (syn. *Rhodosporidium paludigenum*) |
| J Strain 1 | Y-17302 | 67-67 | *Rhodosporidiobolus ruineniae* (syn. *Sporidiobolus ruineniae*) |
| J Strain 3 | | 10-1109 | *Rhodosporidiobolus ruineniae* (syn. *Sporidiobolus ruineniae*) |
| *P. bogoriensis*, (syn. *R. bogoriensis*) | Y-12675 | 67-20 | *Pseudohyphozyma bogoriensis*, (syn. *Rhodotorula bogoriensis*) |
| K | Y-67015 | 08-225 | *Rhodotorula diobovata* (syn. *Rhodosporidium diobovatum*) |
| *S. bombicola* | Y-17069 | 10-162 | *Starmerella bombicola* |
| L | Y-67011 | 68-257 | *Rhodotorula dairenensis* |

Figure 4:
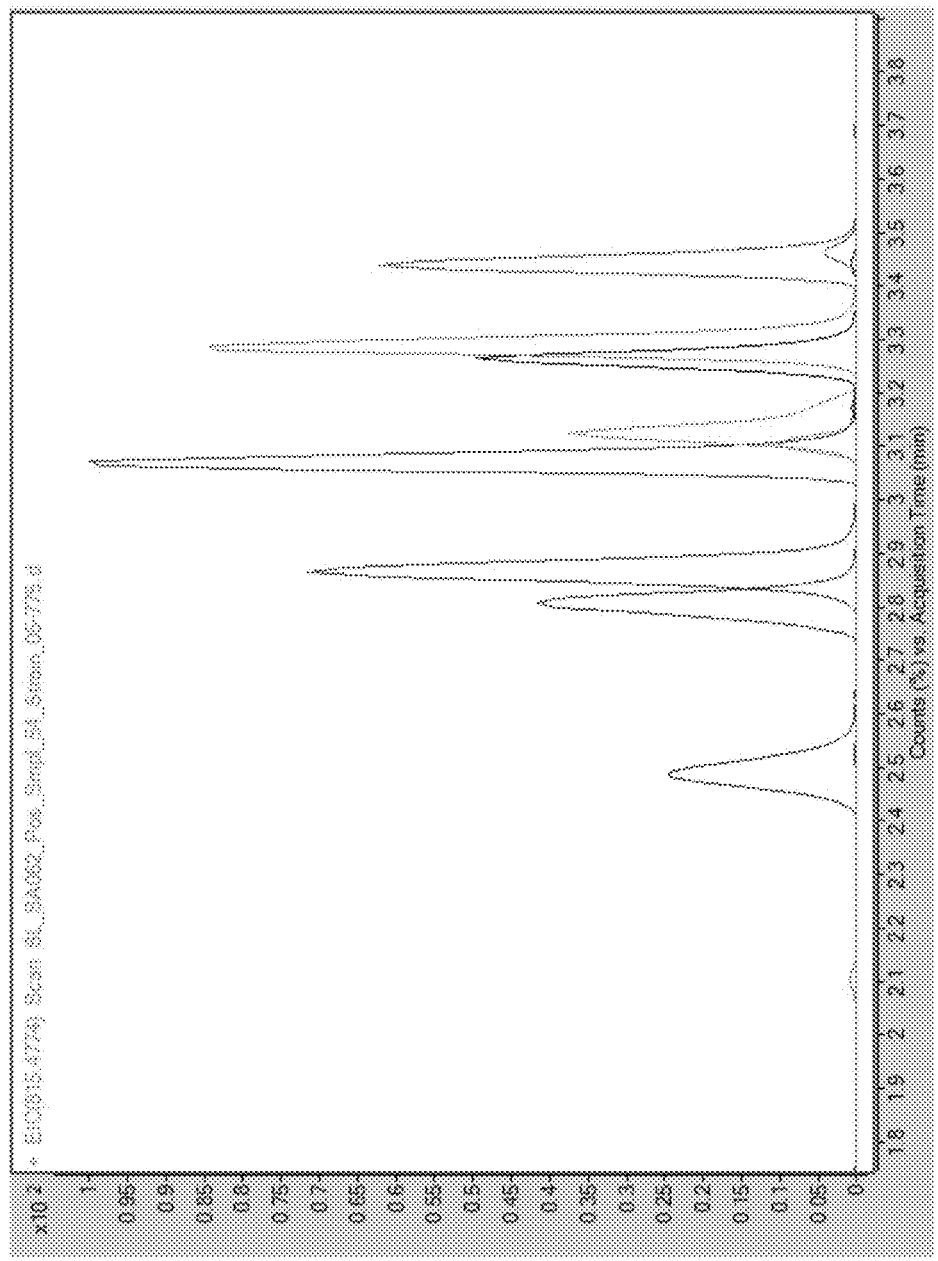
FIG. 4 illustrates an extracted ion chromatograms of extracellular SLs in yeast extract (strain UCDFST 05-775 *Rhodotorula babjevae* (syn. *Rhodosporidium babjevae*)).

\* illustrates the species and Phaff Yeast Culture Collection (UCDFST) strain ID numbers of the yeasts described in FIGS. 2 through 4. Species C strain 2 and Species J strain 3 are not depicted in FIG. 4 because they do not produce extracellular glycolipids.

Example 2

Scaling Up into 7 L (4 L Culture Volume) Fed Batch Fermentors

Yeast strains *Rhodotorula* aff. *paludigena* (syn. *Rhodosporidium* aff. *paludigenum*) (UCDFST 81-84) and *Rhodotorula babjevae* (syn. *Rhodosporidium babjevae*) (UCDFST 04-877) were cultured in 4 L culture volume in batch fermenters. The results are presented in Table 6, below.

TABLE 6

| | UCDFST 04-877 (BATCH) 50 g/L glucose | UCDFST 04-877 (FED BATCH) 150 g/L glucose | UCDFST 81-84 (BATCH) 50 g/L glucose | UCDFST 81-84 (FED BATCH) 150 g/L glucose |
|---|---|---|---|---|
| Dry Cell Weight (g/L) | 16.59 | 32.77 (97.5% up) | 14.39 | 22.71 (36.9% up) |
| Extracellular lipid (g/L) | 3.98 | 7.32 (83.92% up) | 7.69 | 15.22 (97.92% up) |
| Total Microbial production (g/L) | 20.57 (41.1% conversion) | 40.09 (26.73% conversion) | 22.08 (44.16% conversion) | 37.93 (25.28% conversion) |

The results are consistent with the conclusion that increasing amounts of product with increasing amount of carbon source. However, the efficiency with increasing amount of carbon source tends to drop in this particular condition.

In all 4 runs, the growth conditions were as follows: Aeration: 0.5 void volumes per minute (2 L/min), 27+/−1C, Looped RPM with dissolved oxygen to maintain a minimum DO=20% (so agitation ranged from 200-900 RPM), 7 days incubation, pH ranged from 6.3-5.98. In fed-batch runs, 50 of the 150 g/L glucose was fed after 48 hours, throughout a period of 48 hours. Adjusting the glucose concentration and feed rate, and aeration, can increase yields even more.

REFERENCES

1. Asmer, H.-J., et al., Microbial production, structure elucidation and bioconversion of sophorose lipids. Journal of the American Oil Chemists' Society, 1988. 65(9): p. 1460-1466.
2. Lee, K. H. and J. H. Kim, Distribution of substrates carbon in sophorose lipid production by *Torulopsis bombicola*. Biotechnology letters, 1993. 15(3): p. 263-266.
3. Gao, R., et al., Production of sophorolipids with enhanced volumetric productivity by means of high cell density fermentation. Applied microbiology and biotechnology, 2013. 97(3): p. 1103-1111.
4. Asmer, H.-J., et al., Microbial production, structure elucidation and bioconversion of sophorose lipids. J Am Oil Chemists Soc, 1988. 65(9): p. 1460-1466.
5. Cooper, D. and D. Paddock, Production of a biosurfactant from *Torulopsis bombicola*. Appl Environ Microbiol, 1984. 47(1): p. 173-176.
6. Yang, X., et al., Recovery of purified lactonic sophorolipids by spontaneous crystallization during the fermentation of sugarcane molasses with *Candida albicans* O-13-1. Enzyme and microbial technology, 2012. 51(6): p. 348-353.
7. Gorin, P., J. Spencer, and A. Tulloch, Hydroxy fatty acid glycosides of sophorose from *Torulopsis magnoliae*. Canadian Journal of Chemistry, 1961. 39(4): p. 846-855.
8. Tulloch, A. and J. Spencer, Fermentation of long-chain compounds by *Torulopsis apicola*. IV. Products from esters and hydrocarbons with 14 and 15 carbon atoms and from methyl palmitoleate. Canadian Journal of Chemistry, 1968. 46(9): p. 1523-1528.
9. Konishi, M., et al., Production of new types of sophorolipids by *Candida batistae*. Journal of oleo science, 2008. 57(6): p. 359-369.
10. Imura, T., et al., Enzymatic conversion of diacetylated sophoroselipid into acetylated glucoselipid: surface-active properties of novel bolaform biosurfactants. Journal of oleo science, 2010. 59(9): p. 495-501.
11. Jones, D., Novel macrocyclic glycolipids from *Torulopsis gropengiesseri*. Journal of the Chemical Society C: Organic, 1967: p. 479-484.
12. Kurtzman, C. P., et al., Production of sophorolipid biosurfactants by multiple species of the *Starmerella* (*Candida*) *bombicola* yeast clade. FEMS Microbiology Letters, 2010. 311(2): p. 140-146.
13. Kurtzman, C. P., *Candida kuoi* sp. nov., an anamorphic species of the *Starmerella* yeast clade that synthesizes sophorolipids. International Journal of Systematic and Evolutionary Microbiology, 2012. 62(Pt 9): p. 2307-2311.
14. Poomtien, J., et al., Production and Characterization of a Biosurfactant from Cyberlindnera samutprakarnensis JP52T. Bioscience, biotechnology, and biochemistry, 2013. 77(12): p. 2362-2370.
15. Tulloch, A., J. Spencer, and M. Deinema, A new hydroxy fatty acid sophoroside from *Candida bogoriensis*. Canadian Journal of Chemistry, 1968. 46(3): p. 345-348.
16. Spencer, J., P. Gorin, and A. Tulloch, *Torulopsis bombicola* sp. n. Antonie van Leeuwenhoek, 1970. 36(1): p. 129-133.
17. Van Bogaert, I. N., et al., Microbial production and application of sophorolipids. Applied microbiology and biotechnology, 2007. 76(1): p. 23-34.
18. Van Bogaert, I. N., J. Zhang, and W. Soetaert, Microbial synthesis of sophorolipids. Process Biochemistry, 2011. 46(4): p. 821-833.
19. ROSA, C. A. and M.-A. LACHANCE, The yeast genus *Starmerella* gen. nov. and *Starmerella bombicola* sp. nov., the teleomorph of *Candida bombicola* (Spencer, Gorin & Tullock) Meyer & Yarrow. International journal of systematic bacteriology, 1998. 48(4): p. 1413-1417.
20. Chen, J., et al., Production, structure elucidation and anticancer properties of sophorolipid from *Wickerhamiella domercqiae*. Enzyme and microbial technology, 2006. 39(3): p. 501-506.
21. Thaniyavarn, J., et al., Production of sophorolipid biosurfactant by *Pichia anomala*. Bioscience, biotechnology, and biochemistry, 2008. 72(8): p. 2061-2068.
22. Cooper, D. G. and D. A. Paddock, *Torulopsis petrophilum* and surface activity. Applied and environmental microbiology, 1983. 46(6): p. 1426-1429.
23. Kurtzman, C., J. W. Fell, and T. Boekhout, The yeasts: a taxonomic study. Vol. 1. 2011: Elsevier.
24. Fell, J. W., et al., Biodiversity and systematics of basidiomycetous yeasts as determined by large-subunit rDNA D1/D2 domain sequence analysis. International Journal of Systematic and Evolutionary Microbiology, 2000. 50(3): p. 1351-1371.
25. Scorzetti, G., et al., Systematics of basidiomycetous yeasts: a comparison of large subunit D1/D2 and internal transcribed spacer rDNA regions. FEMS yeast research, 2002. 2(4): p. 495-517.
26. Goffeau, A., et al., Life with 6000 genes. Science, 1996. 275(5303): p. 1051-1052.
27. Van Bogaert, I. N., et al., Development of a transformation and selection system for the glycolipid-producing yeast *Candida bombicola*. Yeast, 2008. 25(4): p. 273-278.
28. Van Bogaert, I. N., et al., The biosynthetic gene cluster for sophorolipids: a biotechnological interesting biosurfactant produced by *Starmerella bombicola*. Molecular microbiology, 2013.
29. Kurtzman, C., J. Fell, and T. Boekhout, The Yeasts: A Taxonomic Study. 5th ed. 2011, Amsterdam: Elsevier. 2080.
30. Suutari, M., P. Priha, and S. Laakso, Temperature shifts in regulation of lipids accumulated by *Lipomyces starkeyi*. J. Am. Oil Chem. Soc., 1993. 70: p. 891-894.
31. Sitepu, I., et al., An improved high-throughput Nile red fluorescence assay for estimating intracellular lipids in a variety of yeast species. Journal of Microbiological Methods, 2012. 91(2): p. 321-328.
32. Sitepu, I. R., et al., Manipulation of culture conditions alters lipid content and fatty acid profiles of a wide variety of known and new oleaginous yeasts species. Bioresource Technology, 2013. 144: p. 360-369.
33. Deinema, M., Intra- and Extra-Cellular Lipid Production By Yeasts, 1961, Laboratory of Microbiology, Agricultural University, Wageningen, The Netherlands: Wageningen, Nederland. p. 1-52.

34. Nuñez, A., et al., LC/MS analysis and lipase modification of the sophorolipids produced by *Rhodotorula bogoriensis\*\**. Biotechnology letters, 2004. 26(13): p. 1087-1093.
35. Stodola, F., M. Deinema, and J. Spencer, Extracelluar Lipids of Yeast, in Bacteriological Reviews. 1967, American Society for Microbiology: Baltimore. p. 194-213.
36. Tulloch, A., J. Spencer, and M. Dieinema, A new hydroxy fatty acid sophoroside from *Candida bogoriensis*. Can J Microbiol, 1968. 46(3): p. 345-348.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing one or more glycolipids, comprising:
    a) culturing a population of yeast cells in a yeast cell culture comprising one or more hydrophilic carbon sources, minimum dissolved oxygen of 20%, and a carbon to nitrogen ratio of about 10:1 to about 200:1, wherein the yeast cells are from genera classified within the taxonomic order Sporidiobolales selected from the group consisting of *Rhodotorula* and *Rhodosporidiobolus*, wherein the culture does not comprise one or more hydrophobic carbon sources, and
    b) harvesting the one or more glycolipids secreted into the medium.
2. The method of claim 1, wherein additional hydrophilic carbon source is added.
3. The method of claim 1, wherein the culture comprises less than about 2% (w/v) nitrogen.
4. The method of claim 1, wherein the culture comprises about 0.05% (w/v) ammonium chloride.
5. The method of claim 1, wherein the culture comprises one or more hydrophilic carbon sources at a concentration in the range of about 0.2% (w/v) to about 70% (w/v).
6. The method of claim 1, wherein the hydrophilic carbon source is selected from the group consisting of monosaccharides, oligosaccharides, polysaccharides, sugar alcohols, organic acids, esters, aldehydes, ketones, alcohols, and mixtures thereof.
7. The method of claim 1, wherein the hydrophilic carbon source is a monosaccharide, an oligosaccharide or a polysaccharide and comprises one or more sugar moieties selected from the group consisting of glucose, sucrose, xylose, galactose, rhamnose, arabinose, mannose, cellobiose, galacturonic acid, lactose, sophorose, and mixtures thereof.
8. The method of claim 1, wherein the population of yeast cells comprises one or more species selected from the group consisting of *Rhodotorula babjevae, Rhodotorula diobovata, Rhodotorula kratochvilovae, Rhodotorula paludigena, Rhodotorula* aff. *paludigena, Rhodotorula sphaerocarpa, Rhodosporidiobolus* aff. *colostri, Rhodotorula dairenensis, Rhodosporidiobolus ruineniae,* and *Rhodosporidiobolus* aff. *nylandii*.
9. The method of claim 1, wherein the population of yeast cells comprises one or more strains selected from the group consisting of:
    a) *Rhodotorula babjevae* strain NRRL Y-67018 (UCDFST 04-877),
    b) *Rhodotorula babjevae* strain NRRL Y-67017 (UCDFST 05-775),
    c) *Rhodotorula diobovata* strain NRRL Y-67015 (UCDFST 08-225),
    d) *Rhodotorula kratochvilovae* strain NRRL Y-67016 (UCDFST 05-632),
    e) *Rhodotorula paludigena* strain NRRL Y-67012 (UCDFST 09-163),
    f) *Rhodotorula* aff. *paludigena* strain NRRL Y-67009 (UCDFST 81-84),
    g) strain NRRL Y-67010 (UCDFST 68-43),
    h) *Rhodosporidiobolus* aff. *colostri* strain NRRL Y-67014 (UCDFST 06-583),
    i) *Rhodotorula dairenensis* strain NRRL Y-67011 (UCDFST 68-257),
    j) *Rhodosporidiobolus* aff. *nylandii* strain NRRL Y-67013 (UCDFST 09-1303), and
    k) *Rhodosporidiobolus ruineniae* strain NRRL Y-17302 (UCDFST 67-67).
10. The method of claim 1, wherein the glycolipid comprises a fatty acid comprising from 14 to 24 carbon atoms in length.
11. The method of claim 1, wherein the glycolipid sugar moiety or glycan is monoacetylated or diacetylated.
12. The method of claim 1, further comprising purifying and/or isolating the glycolipid.
13. The method of claim 12, wherein the glycolipid can be purified and/or isolated without cell lysis.
14. The method of claim 1, wherein the method is performed as a batch, fed batch or continuous-feed process.
15. The method of claim 1, wherein the carbon to nitrogen ratio is about 20:1 to about 100:1, or from about 25:1 to about 75:1.
16. The method of claim 1, wherein at least about 2 g/L to about 12 g/L glycolipid is produced.
17. The method of claim 1, wherein the culture comprises one or more hydrophilic carbon sources at a concentration in the range of about 20% (w/v) to about 70% (w/v).
18. The method of claim 1, wherein at least about 1 g/L glycolipid is produced.
19. The method of claim 1, wherein the yeast cells secrete the one or more glycolipids into the medium in a form that can be harvested without solvent extraction.
20. The method of claim 1, wherein the culture does not comprise one or more hydrophobic carbon sources selected from the group consisting of oils, alkanes, fatty acids, fatty esters and mixtures thereof.
21. The method of claim 1, wherein the yeast cells are cultured in baffled shake flasks at a temperature of about 24° C. with continuous agitation for time period sufficient for yeast cell growth and glycolipid production and secretion.
22. A method of producing one or more glycolipids, comprising:
    a) culturing a population of yeast cells in a yeast cell culture comprising one or more hydrophilic carbon sources, minimum dissolved oxygen of 20%, and a carbon to nitrogen ratio of about 10:1 to about 200:1, wherein the population of yeast cells are from a species selected from the group consisting of: *Rhodotorula babjevae, Rhodotorula diobovata, Rhodotorula kratochvilovae, Rhodotorula paludigena, Rhodotorula* aff. *paludigena, Rhodotorula sphaerocarpa, Rhodosporidiobolus* aff. *colostri, Rhodosporidiobolus ruineniae,* and *Rhodosporidiobolus* aff. *nylandii*; and
    b) harvesting the one or more glycolipids secreted into the medium, wherein at least about 1 g/L glycolipid is produced.

23. The method of claim 22, wherein the culture does not comprise one or more hydrophobic carbon sources.

24. The method of claim 23, wherein the culture does not comprise one or more hydrophobic carbon sources selected from the group consisting of oils, alkanes, fatty acids, fatty esters and mixtures thereof.

25. The method of claim 22, wherein an additional hydrophilic carbon source is added.

26. The method of claim 22, wherein the culture comprises less than about 2% (w/v) nitrogen.

27. The method of claim 22, wherein the culture comprises about 0.05% (w/v) ammonium chloride.

28. The method of claim 22, wherein the culture comprises one or more hydrophilic carbon sources at a concentration in the range of about 0.2% (w/v) to about 70% (w/v).

29. The method of claim 22, wherein the hydrophilic carbon source is selected from the group consisting of monosaccharides, oligosaccharides, polysaccharides, sugar alcohols, organic acids, esters, aldehydes, ketones, alcohols, and mixtures thereof.

30. The method of claim 22, wherein the hydrophilic carbon source is a monosaccharide, an oligosaccharide or a polysaccharide and comprises one or more sugar moieties selected from the group consisting of glucose, sucrose, xylose, galactose, rhamnose, arabinose, mannose, cellobiose, galacturonic acid, lactose, sophorose, and mixtures thereof.

31. The method of claim 22, wherein the population of yeast cells comprises one or more strains selected from the group consisting of:
   a) *Rhodotorula babjevae* strain NRRL Y-67018 (UCDFST 04-877),
   b) *Rhodotorula babjevae* strain NRRL Y-67017 (UCDFST 05-775),
   c) *Rhodotorula diobovata* strain NRRL Y-67015 (UCDFST 08-225),
   d) *Rhodotorula kratochvilovae* strain NRRL Y-67016 (UCDFST 05-632),
   e) *Rhodotorula paludigena* strain NRRL Y-67012 (UCDFST 09-163),
   f) *Rhodotorula* aff. *paludigena* strain NRRL Y-67009 (UCDFST 81-84),
   g) *Rhodotorula sphaerocarpa* strain NRRL Y-67010 (UCDFST 68-43),
   h) *Rhodosporidiobolus* aff. *colostri* strain NRRL Y-67014 (UCDFST 06-583),
   i) *Rhodosporidiobolus* aff. *nylandii* strain NRRL Y-67013 (UCDFST 09-1303), and
   k) *Rhodosporidiobolus ruineniae* strain NRRL Y-17302 (UCDFST 67-67).

32. The method of claim 22, wherein the glycolipid comprises a fatty acid comprising from 14 to 24 carbon atoms in length.

33. The method of claim 22, wherein the glycolipid sugar moiety or glycan is monoacetylated or diacetylated.

34. The method of claim 22, further comprising purifying and/or isolating the glycolipid.

35. The method of claim 22, wherein the glycolipid can be purified and/or isolated without cell lysis.

36. The method of claim 22, wherein the method is performed as a batch, fed batch or continuous-feed process.

37. The method of claim 22, wherein the carbon to nitrogen ratio is about 20:1 to about 100:1, or from about 25:1 to about 75:1.

38. The method of claim 22, wherein at least about 2 g/L to about 12 g/L glycolipid is produced.

39. The method of claim 22, wherein the culture comprises one or more hydrophilic carbon sources at a concentration in the range of about 20% (w/v) to about 70% (w/v).

40. The method of claim 22, wherein the yeast cells secrete the one or more glycolipids into the medium in a form that can be harvested without solvent extraction.

* * * * *